(12) United States Patent
Shirota et al.

(10) Patent No.: US 6,294,073 B1
(45) Date of Patent: Sep. 25, 2001

(54) MANUFACTURING METHOD AND APPARATUS OF ALKALINE IONIZED WATER

(75) Inventors: Kazuhiro Shirota; Akira Isaka, both of Urayasu (JP)

(73) Assignee: Chemicoat & Co., Ltd., Chiba (JP)

( * ) Notice: Subject to any disclaimer, the term of this patent is extended or adjusted under 35 U.S.C. 154(b) by 0 days.

(21) Appl. No.: 09/175,185

(22) Filed: Oct. 20, 1998

(30) Foreign Application Priority Data

Oct. 22, 1997 (JP) ...................................... 9-326896
Dec. 24, 1997 (JP) ...................................... 9-365938

(51) Int. Cl.$^7$ .................................................. C02F 1/461
(52) U.S. Cl. ............................................................ 205/749
(58) Field of Search ................................... 205/746, 749, 205/349; 204/257, 263, 237

(56) References Cited

U.S. PATENT DOCUMENTS 5,833,831 * 11/1998 Kitajima et al. ...................... 205/349

* cited by examiner

Primary Examiner—Kathryn Gorgos
Assistant Examiner—Thomas H Parsons
(74) Attorney, Agent, or Firm—Michael J. Striker

(57) ABSTRACT

A manufacturing method and apparatus of strongly alkaline ionized water exceeding pH 12.0 by electrolysis of water. As an electrolysis solution supplied to a cathode cell of an electrolytic bath, alkaline ionized water produced in the cathode cell is used, and an operation, in which the alkaline ionized water produced in the cathode cell is circulated and supplied to the cathode cell and is subjected to application of electrolytic voltage, is repeated, so that a cation is accumulated to increase the pH value. As a method for circulating and supplying the alkaline ionized water produced in the cathode cell to the cathode cell, a circulation container bath is used, and the circulation container bath and the cathode cell of the electrolytic bath are connected via a circulating line containing a circulating pump. The circulation container bath has a withdrawing system containing a water collecting device for withdrawing alkaline ionized water having a desired pH value to the outside.

2 Claims, 12 Drawing Sheets

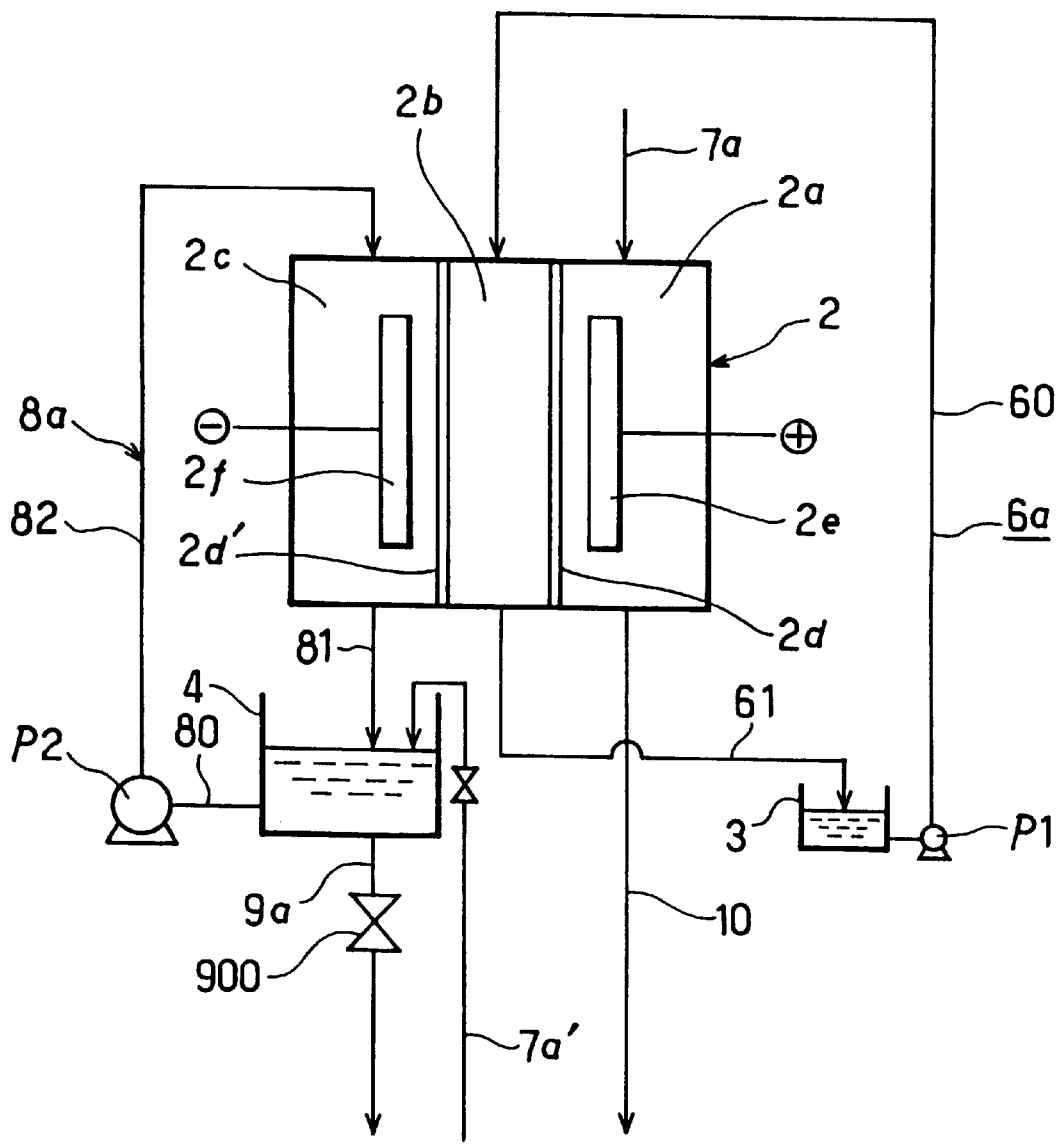
Fig. 1-A

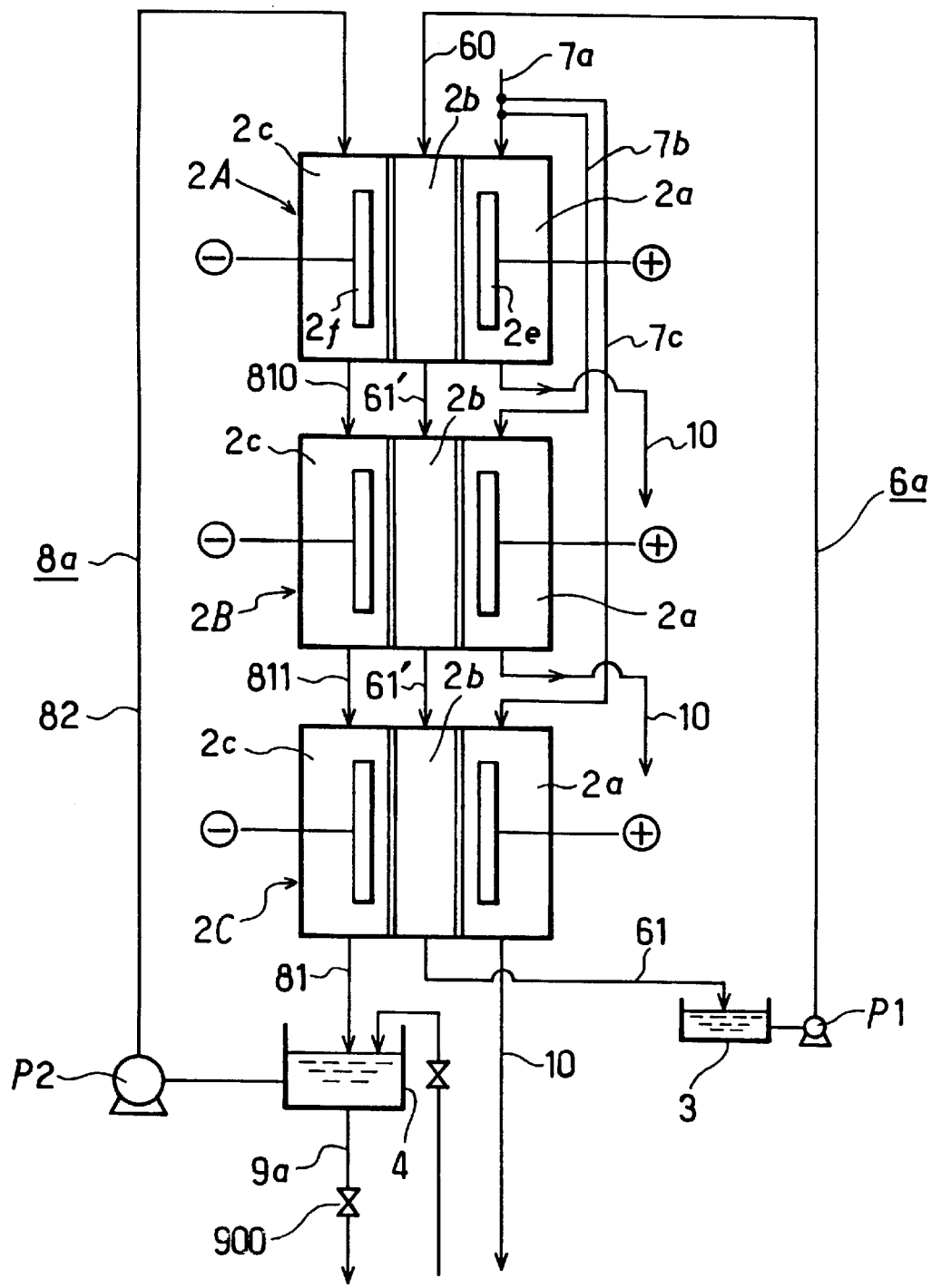
Fig.1-B

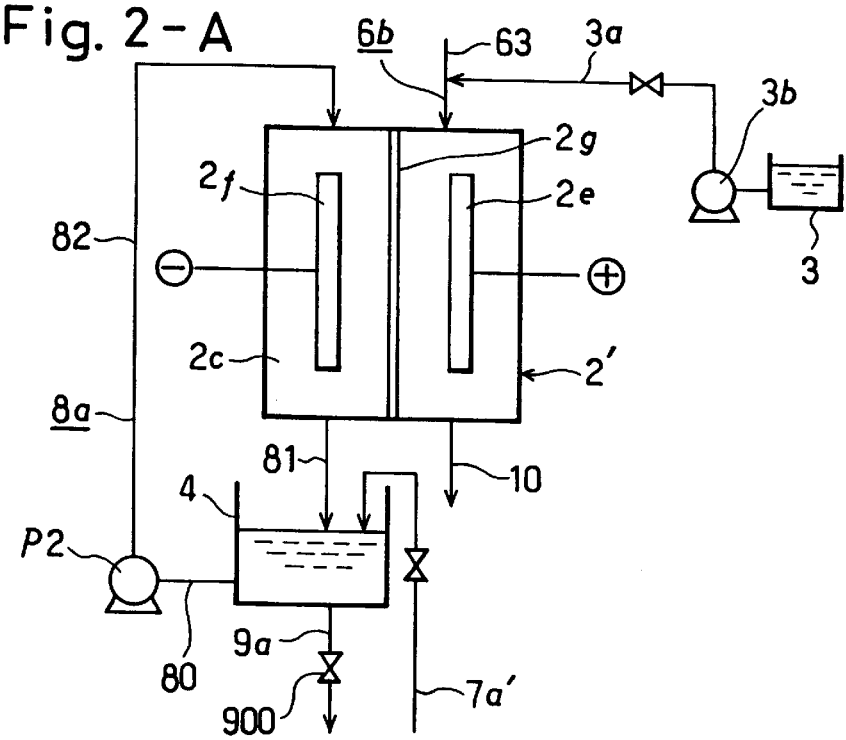
Fig. 2-A
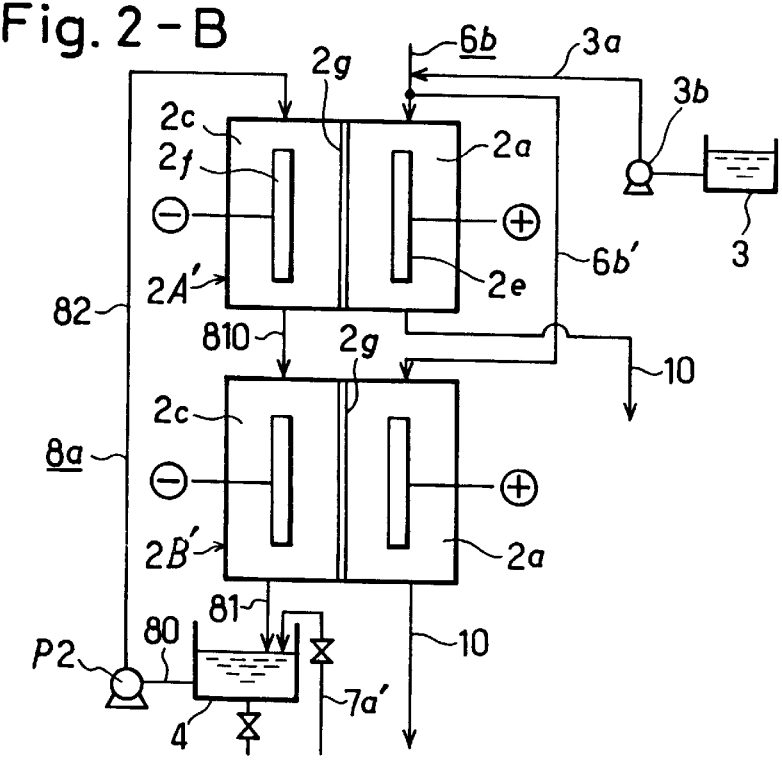
Fig. 2-B

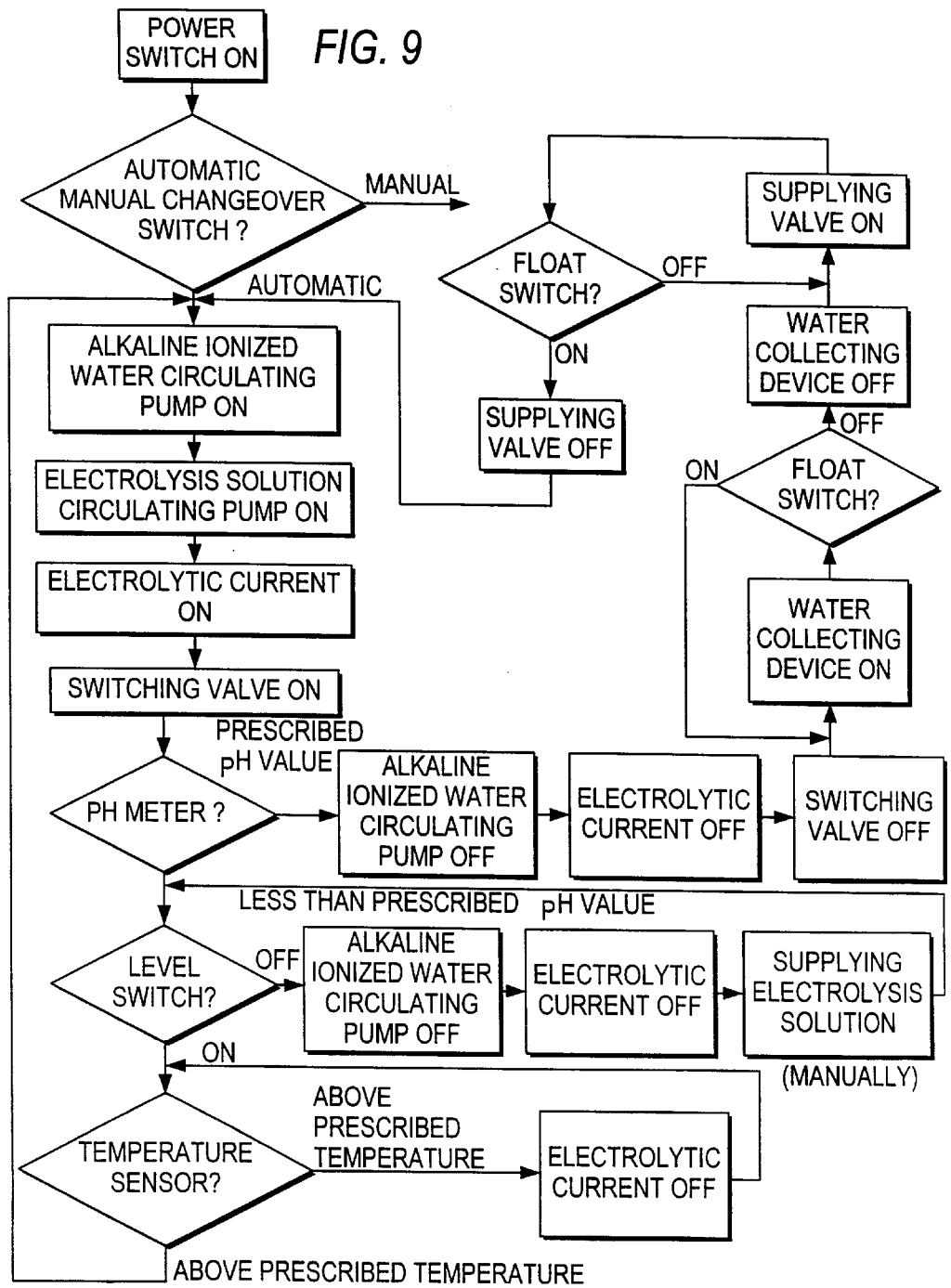

Fig.10-A
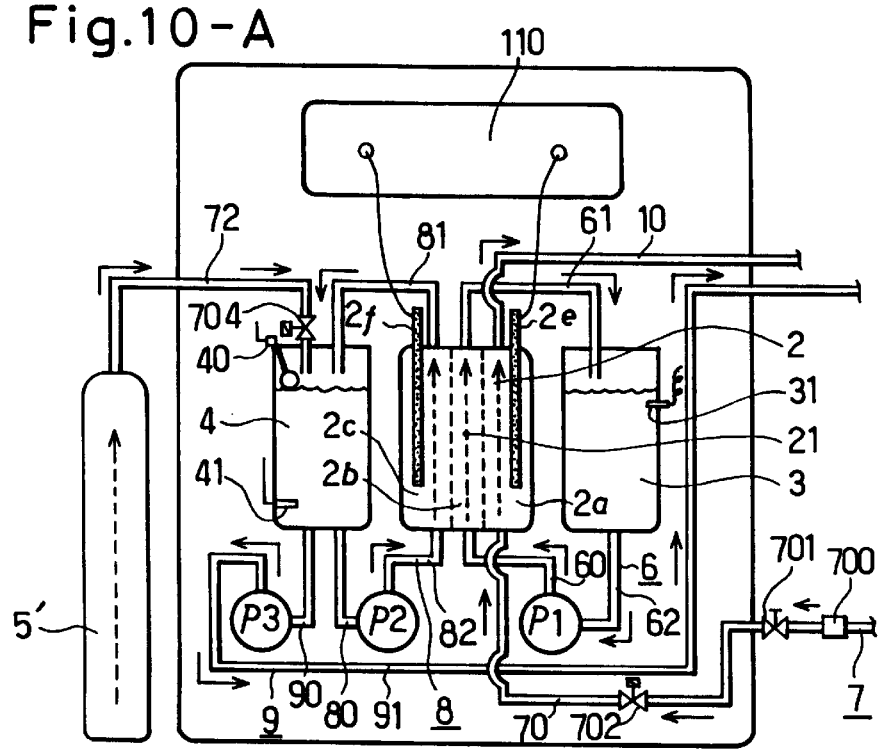
Fig.10-B
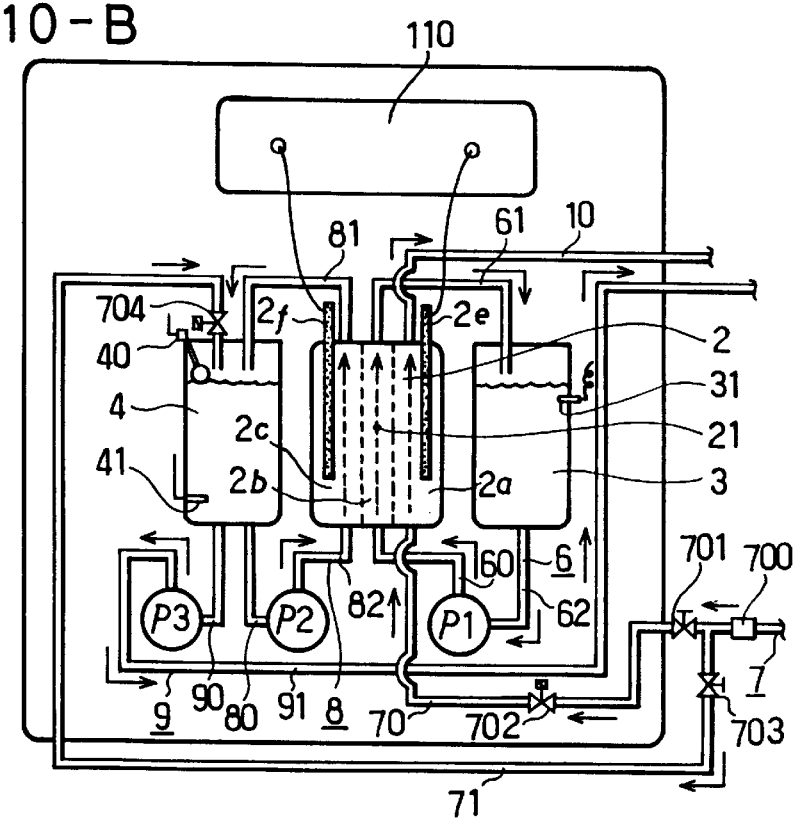

MANUFACTURING METHOD AND APPARATUS OF ALKALINE IONIZED WATER

BACKGROUND OF THE INVENTION

1. Field of the Invention

The present invention relates to electrolytic ionized water, and more specifically, relates to a manufacturing method and an apparatus of strongly alkaline ionized water.

2. Description of the Related Art

Alkaline water produced by electrolysis of water, i.e., alkaline ionized water, has been known. As an apparatus and a method for producing the alkaline ionized water, a continuous method has been known, in which alkaline water is produced by continuously supplying an electrolysis solution to an electrolytic bath. The conventional technique can be roughly classified into the following two methods.

One of them uses an electrolytic bath having a three-cell configuration. That is, the electrolytic bath is separated by two diaphragms to have an electrolysis solution cell at the center, having on both sides an anode cell and a cathode cell, and electrodes provided in both the anode cell and the cathode cell. A supplying line of tap water or pure water is connected to inlets of the anode cell and the cathode cell, a withdrawing line of acidic water is connected to an outlet of the anode cell, and a withdrawing line of alkaline ionized water is connected to an outlet of the cathode cell. An electrolysis solution bath is provided outside, and its outlet is connected to an inlet of the electrolysis solution cell via a circulating pump, so that the electrolysis solution is circulated and supplied to the electrolysis solution cell.

The other one of them uses an electrolytic bath having a two-cell configuration. Specifically, an electrolytic bath is separated by one diaphragm to an anode cell and a cathode cell. A supplying line of an electrolysis solution is connected to inlets of the anode cell and the cathode cell, a withdrawing line of acidic water is connected to an outlet of the anode cell, and a withdrawing line of alkaline ionized water is connected to an outlet of the cathode cell.

In the conventional technique, a large amount of water can be produced by continuously supplying an electrolysis solution to an electrolytic bath to simultaneously obtain alkaline ionized water and acidic water, but there are the following problems.

The first problem is that it is difficult to produce, without any problem, alkaline ionized water having a high pH value. In the case where an electrolytic bath having the two-bath configuration, the electrolysis solution is continuously exhausted from the outlet through the cathode cell of a path form, and therefore the time where an electrolytic voltage is applied to the electrolysis solution is a period where the electrolysis solution passes between the electrodes, which is extremely short.

In the case where an electrolytic bath having the three-cell configuration, an electrolysis solution in the central electrolysis solution cell is electrolyzed to transfer a cation to water in the cathode cell through the diaphragm to produce alkaline ionized water. Since raw material water (tap water or pure water) supplied from an inlet of the cathode cell is continuously exhausted from an outlet of the cathode cell through the cathode cell of a path form, the cation is transferred from the electrolysis solution to the raw material water in an extremely short period of time where the raw material water passes between the electrodes.

In both cases, therefore, the pH value of the alkaline ionized water thus produced becomes low. Accordingly, alkaline ionized water for drinking can be produced, but it is difficult to produce water having a high pH value, which is effective as a detergent and a disinfectant.

When the concentration of the electrolysis solution is increased as a countermeasure against the problem, an electrolysis solution containing a chloride ion in a high concentration is electrolyzed, and a problem arises in that a large amount of gas having a strong irritative smell is generated on the side of the anode cell. When the supplying amount of tap water or pure water is reduced as another countermeasure against the problem, a part of the electric energy for electrolysis is converted into heat energy to increase the temperature of the electrolysis solution, and electrolysis for a long period of time cannot be conducted due to the load on the diaphragm. Therefore, even when an electrolytic bath having the three-cell configuration, in which an electrolysis solution of a high concentration can be used, is used, the pH value of alkaline ionized water that can be industrially produced is 12.0 or less.

The second problem is that when an electrolytic bath having the three-cell configuration is used, and pure water is used as raw material water considering the quality of alkaline ionized water, the pure water is also used for the production of the by-product acidic water. Since pure water is relatively costly water, from which anions and cations are removed, the production cost of the alkaline ionized water is increased.

The third problem is that the pH value of the thus produced alkaline ionized water widely varies, and it is difficult to stably produce alkaline water having a constant pH value. That is, in the conventional technique, the electrolytic current changes depending on the change of the concentration of the electrolysis solution and the change of the liquid temperature, and unevenness is enhanced, for example, alkaline ionized water having a high pH value or alkaline ionized water having a low pH value is obtained in summer or in winter.

The production method of alkaline ionized water includes a batch method, in addition to the continuous methods. In this method, an electrolysis solution stored in an electrolytic bath is electrolyzed in a period of time to produce alkaline ionized water, and the resulting alkaline ionized water is withdrawn from the electrolytic bath. Thereafter, an electrolysis solution is again stored in the electrolytic bath to be electrolyzed in a period of time.

In this conventional technique, since an electrolytic voltage is applied under the conditions in that the electrolysis solution is stored in the electrolytic bath, alkaline ionized water has a higher pH value than in the case of the continuous method by arbitrarily setting the time of applying voltage. However, it involves problems in that since the capacities of the cathode cell and the anode cell of the electrolytic bath are limited, the ratio of production amounts of alkaline ionized water and acidic water cannot be arbitrarily changed; the pH values of alkaline ionized water and acidic water cannot be freely controlled; and in order to produce large amounts of alkaline ionized water and acidic water, the electrolytic bath storing the electrolysis solution and its incidental equipment must be large scaled, resulting in that the whole apparatus becomes large scaled.

DESCRIPTION OF THE INVENTION

The first object of the invention is to provide a novel manufacturing method of electrolytic ionized water, by which alkaline ionized water having strong alkaline nature of pH 12.0 or higher and having a pH value with less fluctuation can be mass-produced.

The second object of the invention is to provide a compact and small apparatus of manufacturing that can stably and efficiently mass-produce alkaline ionized water having strong alkaline nature and having a pH value with less fluctuation.

The third object of the invention is to provide a compact and small apparatus that can automatically mass-produce alkaline ionized water having a desired pH value with high efficiency.

The fourth object of the invention is to provide an apparatus that can efficiently mass-produce alkaline ionized water having strong alkaline nature and having a pH value with less fluctuation, and can automatically sell it in a quantitative manner.

The manufacturing method of electrolytic ionized water of the invention to attain the first object comprises applying an electrolytic voltage between a cathode electrode and an anode electrode inside an electrolytic bath with continuously supplying an aqueous solution containing an electrolyte to the electrolytic bath, so as to produce alkaline ionized water through electrolysis of the aqueous solution containing an electrolyte, characterized in that alkaline ionized water is produced in a cathode cell of the electrolytic bath, and an operation, where the alkaline ionized water thus obtained is again supplied to the cathode cell and is subjected to application of electrolytic voltage, is repeated to accumulate a cation, to increase a pH value of the alkaline ionized water.

This method is a circulating electrolysis system, in which alkaline ionized water produced in the cathode cell is used as an electrolysis solution, and an operation, where it is again supplied to the cathode cell to be electrolyzed, is repeated. Therefore, strongly alkaline ionized water having a pH value exceeding 12.0, for example, pH 14, can be stably produced by adjusting the application time of the electrolytic voltage even under the conditions of low voltage and a low current.

According to the invention, the pH value of the alkaline ionized water is increased by circulating and using the alkaline ionized water produced in the cathode cell as an electrolysis solution, and therefore alkaline ionized water of high quality with less fluctuation of its pH value can be produced. Similar to the conventional continuous method, the ratio of production amounts of the alkaline ionized water and the acidic water produced can be arbitrarily changed, and the pH values of the alkaline ionized water and the acidic water can be freely set.

In the manufacturing method of electrolytic ionized water of the invention, preferably, an electrolytic bath having a three-cell configuration having a cathode cell, an intermediate cell and an anode cell, which are separated by a pair of diaphragms, is used; raw material water for production of acidic water is supplied to the anode cell; and an electrolysis solution is circulated and supplied to the intermediate cell. Supply of alkaline ionized water produced in the cathode cell to the cathode cell is carried out with a circulation system, in which the alkaline ionized water is withdrawn from the cathode cell and supplied to the cathode cell by a pump, with storing the same in a container equipped outside the electrolytic bath.

The invention involves not only the case of a single electrolytic bath, but also the cases using plural electrolytic baths. That is, plural electrolytic baths each having the three-cell configuration having a cathode cell, an intermediate cell and an anode cell, which are separated by a pair of diaphragms, are used in series; raw material water for production of acidic water is supplied to the anode cell of each of the electrolytic baths; and an electrolysis solution is circulated and supplied to the intermediate cell of each of the electrolytic bath. Supply of alkaline ionized water produced in the cathode cell to the cathode cell is carried out with an circulation system, in which the alkaline ionized water withdrawn from the cathode cell of the uppermost electrolytic bath is successively supplied to the cathode cell of the next lower electrolytic bath, and the alkaline ionized water withdrawn from the cathode cell of the lowermost electrolytic bath is supplied to the cathode cell of the uppermost electrolytic bath by a pump, with storing the same in a container equipped outside the electrolytic baths.

According to this embodiment, alkaline ionized water having a high pH value can be produced in a shorter period of time.

The manufacturing method of electrolytic ionized water of the invention involves the case using an electrolytic bath having a two-cell configuration. That is, an electrolytic bath having the two-cell configuration having a cathode cell and an anode cell, which are separated by a diaphragm, is used; an electrolysis solution is supplied to the cathode cell and the anode cell; and supply of the alkaline ionized water produced in the cathode cell to the cathode cell is carried out by a circulating system, in which the alkaline ionized water is withdrawn from the cathode cell and supplied to the cathode cell by a pump, with storing the same in a container equipped outside the electrolytic bath.

This method involves the case where plural electrolytic baths are used. That is, plural electrolytic baths each having the two-cell configuration having a cathode cell and an anode cell, which are separated by a diaphragm, are used in series, and an electrolysis solution is supplied to the anode cell of each of the electrolytic baths. An electrolysis solution is used as raw material water for producing alkaline ionized water, and supply of alkaline ionized water produced in the cathode cell to the cathode cell is carried out with an circulation system, in which the alkaline ionized water withdrawn from the cathode cell of the uppermost electrolytic bath is supplied to the cathode cell of the next lower electrolytic bath, and the alkaline ionized water withdrawn from the cathode cell of the lowermost electrolytic bath is supplied to the cathode cell of the uppermost electrolytic bath by a pump, with storing the same in a container equipped outside the electrolytic baths.

The manufacturing apparatus of electrolytic ionized water of the invention for attaining the second object is characterized by comprising an circulation container of alkaline ionized water, in addition to an electrolytic bath and an electrolysis solution bath in a box, and comprising a circulating pump for alkaline ionized water, in addition to a pump circulating the electrolysis solution. The electrolytic bath comprises a cathode cell, an intermediate cell and an anode cell, which are separated by a pair of diaphragms; an anode electrode is equipped in the anode cell; and a cathode electrode is equipped in the cathode cell. The electrolysis solution bath is connected to the intermediate cell of the electrolytic bath via an electrolysis solution circulating line containing the electrolysis solution circulating pump. The circulation container of alkaline ionized water and the cathode cell of the electrolytic bath are connected to each other via a circulating line containing the circulating pump. The circulation container is equipped with a means for supplying raw material water of alkaline ionized water having a makeup valve, and the circulation container of alkaline ionized water is equipped with a withdrawing line containing water collecting device for alkaline ionized water having a desired pH value.

According to this constitution, the apparatus becomes compact, in which alkaline ionized water produced in the cathode cell is circulated and used as an electrolysis solution to attain a high pH value.

The manufacturing apparatus of electrolytic ionized water involves not only the case of a single electrolytic bath, but also the cases using plural electrolytic baths. In this case, the intermediate cells of the plural electrolytic baths are connected to each other via a line, and the intermediate cell of the lowermost electrolytic baths and the intermediate cell of the uppermost electrolytic baths are connected to each other via an electrolysis solution circulating line containing an electrolysis solution circulating pump. A raw material water supplying line is connected to the anode cell of each of the electrolytic bath. The cathode cell of each of the electrolytic bath are connected to each other via a line, and the cathode cell of the lowermost electrolytic bath and the cathode cell of the uppermost electrolytic bath are connected to each other via a circulating line containing a circulating pump.

In addition to the above constitution, the invention further comprises, in order to attain the third object, a controlling means. The controlling means comprises, in addition to a direct-current power source for the anode electrode and the cathode electrode, at least a controller controlling the electrolysis solution circulating pump, the circulating pump of the alkaline ionized water, and the water collecting device for alkaline ionized water having a desired pH value.

More preferably, a pH meter for setting a pH value of alkaline ionized water to be produced is used, and the circulation container of alkaline ionized water is equipped with a pH measuring device. The pH meter and the pH measuring device are connected to the controller. Accordingly, at the time when the pH value of the alkaline ionized water in the circulation container reaches the value set by the pH meter, the electrolysis is terminated and the operation of the circulating pump is terminated; in the subsequent step, the water collecting device is operated; and in the further subsequent step, the makeup valve is operated to automatically supply raw material water in an amount corresponding to the loss in weight of the withdrawn alkaline ionized water.

According to this constitution, the quantitative nature of the alkaline ionized water, which is circulated and supplied as an electrolysis solution of the cathode cell and is repeatedly subjected to the application of an electrolytic voltage, is ensured, so as to automatically produce alkaline water having a high pH value with less fluctuation in an industrially stable manner.

In order to attain the fourth object, the invention further comprises, outside the box, a container connected to the withdrawing line of alkaline ionized water, and a withdrawing valve for withdrawing alkaline ionized water contained in the container, the valve being opened by insertion of a coin.

According to this constitution, alkaline water exceeding pH 12.0 with less fluctuation of the pH value can be efficiently mass-produced with a small apparatus, and can be automatically sold in a quantitative manner.

While other characteristics and advantages of the invention will be apparent from the following detailed description, it is apparent that the invention is not construed as being limited to the constitutions shown in the examples unless it has the basic characteristics of the invention, and a person skilled in the art can make various changes and modifications without departing the scope of the invention.

BRIEF DESCRIPTION OF THE DRAWINGS

FIG. 1-A is an explanatory view schematically showing the first embodiment of the manufacturing method and apparatus of electrolytic ionized water according to the invention.

FIG. 1-B is an explanatory view schematically showing another example of the first embodiment of the manufacturing method and apparatus of electrolytic ionized water according to the invention.

FIG. 2-A is an explanatory view schematically showing the second embodiment of the manufacturing method and apparatus of electrolytic ionized water according to the invention.

FIG. 2-B is an explanatory view schematically showing another example of the second embodiment of the manufacturing method and apparatus of electrolytic ionized water according to the invention.

FIG. 9 is a flowchart showing an example of a controlling program of the manufacturing apparatus of electrolytic ionized water according to the invention.

FIG. 10-A is a front view of another example of the supplying system of raw material water for producing alkaline ionized water.

FIG. 10-B is a front view of another example of the supplying system of raw material water for producing alkaline ionized water.

DETAILED DESCRIPTION OF THE INVENTION

Figure 3:
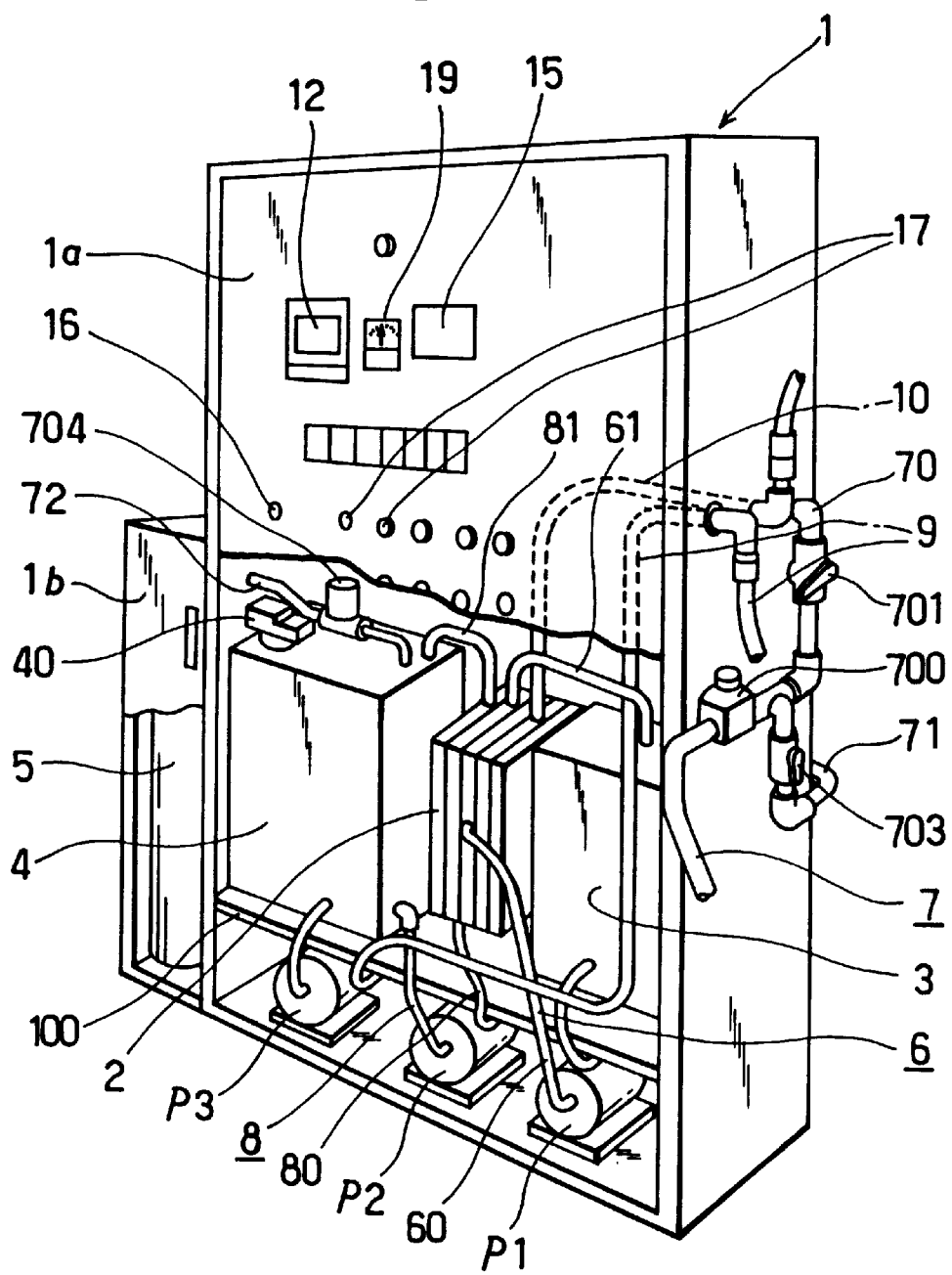
FIG. 3 is a partially cutaway view in perspective of the first example of a manufacturing apparatus of electrolytic ionized water according to the invention.

The invention is described with reference to the attached drawings.

FIG. 1-A shows the summary of the first embodiment of the manufacturing method and apparatus of electrolytic ionized water according to the invention. Numeral 2 denotes an electrolytic bath, which has an intermediate cell 2b to be an electrolysis solution cell at the center, a diaphragm (anion exchange membrane) 2d forming an anode cell 2a at one side of the intermediate cell 2b, and a diaphragm (cation exchange membrane) 2d' forming a cathode cell 2c at the other side. In the anode cell 2a and the cathode cell 2c, an anode electrode 2e and a cathode electrode 2f are provided, respectively, which face each other. The anode electrode 2e and the cathode electrode 2f are connected to a direct-current power source 115 which is shown for example in FIG. 7.

A supplying system 7a of raw material water for producing acidic water is connected to the anode cell 2a, and water selected from water for industrial use, tap water and well water is supplied from it to the anode cell 2a. An acidic water withdrawing system 10 is connected to the other position of the anode cell 2a. An electrolysis solution supplying line 60 is connected to the intermediate cell 2b, to continuously supply the electrolysis solution. An electrolysis solution withdrawing line 61 is connected to the other position of the intermediate cell 2b. The electrolysis solution supplying line 60 and the electrolysis solution withdrawing line 61 are connected to a line having an electrolysis solution bath 3 and a pump P1, and an electrolysis solution circulating system 6a is constituted from them.

The electrolysis solution used herein means a liquid that is electrolyzed into a cation and an anion by the application of electrolytic voltage. In the first embodiment, a saturated solution of sodium chloride can be used as the electrolysis solution. However, taking pumping operation into consideration, a sodium chloride solution of from 10 to 30% is generally used. In order to prevent deposition of calcium ion and magnesium ion, from 1 to 5% of sodium citrate may be added.

A container bath 4 of alkaline ionized water is provided outside the electrolytic bath 2, a circulation system 8a is constituted with the cathode cell 2c of the electrolytic bath 2 by a line containing a circulating pump P2. That is, the container bath 4 is connected at the upper part to a withdrawing line 81 of the cathode cell 2c, and connected at the bottom part to an inlet of the circulating pump P2 via a line 80. An outlet of the circulating pump P2 is connected to the supplying side of the cathode cell 2c via a line 82. The container bath 4 has at the bottom a withdrawing system 9a of alkaline ionized water having a desired pH value, and the withdrawing system 9a has a water collecting means 900. The water collecting means 900 may be arbitrarily selected from, for example, a valve and a pump.

A supplying system 7a' of raw material water for alkaline ionized water is connected to the container bath 4. The raw material water may be tap water. However, taking the quality of alkaline ionized water obtained and maintenance of the apparatus into consideration, water, from which a cation and an anion are removed, i.e., pure water, is preferably used. Also, if pure water is used, the hydroxide ion concentration increases and hence, use of pure water is advantageous, whereby water having a slightly higher pH value can be obtained.

Upon producing alkaline ionized water according to the first embodiment, raw material water for producing acidic water is supplied from the raw material water supplying system 7a to the anode cell 2a; the electrolysis solution is continuously circulated and supplied to the intermediate cell 2b by the circulation system 6a; raw material water for alkaline ionized water, for example, pure water, stored in the container bath 4 is supplied to the cathode cell 2c by the circulating pump P2; and the electrolytic voltage is applied between the anode electrode 2e and the cathode electrode 2f.

By the application of the electrolytic voltage, the electrolysis solution is electrolyzed, an anion (chloride ion) is transferred to the anode cell 2a through the diaphragm 2d, and a cation (sodium ion) is transferred to the cathode cell 2c through the diaphragm 2d'. Accordingly, water in the anode cell becomes acidic, and water in the cathode cell becomes alkaline, to produce alkaline ionized water in the cathode cell 2c.

The alkaline ionized water is exhausted to the container bath 4 through the line 81, and again supplied to the cathode cell 2c by the circulating pump P2 through the line 82, so as to be again electrolyzed by the anode electrode 2e and the cathode electrode 2f.

The above procedures are repeated in the invention. Because alkaline ionized water produced in the cathode cell 2c is circulated and supplied to the cathode cell 2c as an electrolysis solution to be repeatedly electrolyzed by applying electrolytic voltage, the cation is accumulated in the alkaline ionized water in the cathode cell 2c to increase the pH value with the lapse of time. After applying electrolytic voltage for a prescribed period of time to obtain a desired pH value, alkaline ionized water is withdrawn by operating the water collecting means 9a.

On the other hand, water supplied to pass through the anode cell 2a becomes acidic water by electrolysis and is continuously withdrawn to the outside by the acidic water withdrawing system 10.

FIG. 1-B shows another example of the first embodiment of the invention. In this example, plural electrolytic baths 2A, 2B and 2C each having the above-described structure are used (an example using three baths is shown in the figure), and the electrolytic baths 2A, 2B and 2C are connected in series.

A supplying system 7a of raw material water for producing acidic water is connected to an anode cell 2a of the first electrolytic bath 2A, and raw material water for producing acidic water is supplied to the anode cell 2a. A supplying system 7b branched from the supplying system 7a is connected to an anode cell 2a of the second electrolytic bath 2B, and similarly a supplying system 7c branched from the supplying system 7a is connected to an anode cell 2a of the third electrolytic bath 2C.

A supplying line 60 is connected to an inlet of an intermediate cell 2b of the first electrolytic bath 2A, and an electrolysis solution is continuously supplied. An electrolysis solution exhausting line 61' is connected to an outlet of the intermediate cell 2b, and the electrolysis solution exhausting line 61' is connected to an inlet of an intermediate cell 2b of the second electrolytic bath 2B. The electrolysis solution exhausting line 61' of the intermediate cell 2b is connected to an inlet of an intermediate cell 2b of the final electrolytic bath 2C, and an electrolysis solution exhausting line 61 of an outlet of the intermediate cell 2b is connected to the supplying line 60 via a line containing an electrolysis solution bath 3 and a pump P1, so as to form a circulation system 6a of the electrolysis solution.

Cathode cells 2c of the first electrolytic bath 2A, the second electrolytic bath 2B and the third electrolytic bath 2C are connected to each other in series by lines 810 and 811, to form a circulation system 8a via a line containing an outer container bath (container bath for circulation) 4 and a circulating pump P2. That is, the container bath 4 is connected at an upper part to a withdrawing line 81 of the cathode cell 2c of the third electrolytic bath 2C, and is connected at the bottom to an inlet of the circulating pump P2. An outlet of the circulating pump P2 is connected to an inlet of the cathode cell 2c of the first electrolytic bath 2A via a line 82. The container bath 4 has at the bottom a withdrawing system 9a of alkaline ionized water having a desired pH value, and the withdrawing system 9a has a water collecting means 900. The water collecting means 900 may be arbitrarily selected from, for example, a valve and a pump. As similar to the above embodiment, a supplying system 7a' of raw material water of alkaline ionized water is connected to the container bath 4.

In this example, raw material water for producing acidic water is supplied to the anode cells 2a of the electrolytic baths 2A, 2B and 2C via the supplying systems 7a, 7b and 7c, respectively; the electrolysis solution is circulated and supplied to the intermediate cells 2b of the electrolytic baths 2A to 2C via the electrolysis solution circulation system 6a; raw material water of alkaline ionized water previously stored in the container bath 4 is supplied to the cathode cells 2c of the electrolytic baths 2A to 2C in this order by the circulating pump P2; and under the conditions, electrolytic voltage is applied between anode electrodes 2e and cathode electrodes 2f of the electrolytic baths.

In the first electrolytic bath 2A, alkaline ionized water is produced in the cathode cell 2c through the electrolysis as described above. The alkaline ionized water is supplied to the cathode cell 2c of the second electrolytic bath 2B via the line 810. It is similarly electrolyzed in the second electrolytic bath 2B, and a cation is accumulated in the alkaline ionized water. The alkaline ionized water is supplied to the cathode cell 2c of the third electrolytic bath 2C via the line 811, and is again electrolyzed in the third electrolytic bath 2C, so that a cation is further accumulated in the alkaline ionized water. The alkaline ionized water produced in the lowermost electrolytic bath 2C is exhausted from the cathode cell 2c to the container bath 4 via the line 81, and then again supplied to the cathode cell 2c of the first electrolytic bath 2A by the circulating pump P2 via the line 82, which is then again electrolyzed by the anode electrode 2e and the cathode electrode 2f. This operation is repeated in the second electrolytic bath 2B and the third electrolytic bath 2C.

In the embodiment of FIG. 1-B, because the alkaline ionized water produced in the cathode cells 2c of the plural electrolytic baths 2A, 2B and 2C one by another is circulated and supplied as an electrolysis solution, so that electrolytic voltage is repeatedly applied to conduct electrolysis, a cation is accumulated in the alkaline ionized water in a short period of time, and alkaline ionized water having a high pH value can be effectively produced. When the pH value becomes the desired value, the alkaline ionized water is withdrawn by operating the water collecting means 900.

FIG. 2-A shows the summary of the second embodiment of the manufacturing method and apparatus of electrolytic ionized water according to the invention. Numeral 2' denotes an electrolytic bath, which has a diaphragm (ion exchange membrane) 2g at the center. An anode cell 2a is provided on one side of the diaphragm 2g as a boundary, and a cathode cell 2c is provided on the other side. An anode electrode 2e and a cathode electrode :2f are provided in the anode cell 2a and cathode cell 2c, respectively, and face each other. The anode electrode 2e and the cathode electrode 2f are connected to a direct-current power source.

An electrolysis solution supplying system 6b is connected to the anode cell 2a, and an electrolysis solution is supplied to the anode cell 2a. In this example, in the electrolysis solution supplying system 6b, a raw material water supplying line 63 is connected to an electrolysis solution supplying line 3a via a valve, the electrolysis solution supplying line 3a is connected to an electrolysis solution bath 3 via an electrolysis solution supplying pump 3b.

Therefore, raw material water added with an electrolysis solution of a desired concentration (for example, a sodium chloride solution of from 10 to 30%) is supplied as an electrolysis solution to the anode cell 2a. Tap water may be used as the electrolysis solution. In this case, tap water is supplied from the raw material water supplying line 63 with the valve closed. An acidic water withdrawing system 10 is connected to the other position of the anode cell 2a.

On the other hand, a container bath (container bath for circulation) 4 for alkaline ionized water is provided outside the electrolytic bath 2, and a circulation system 8a is constituted with the cathode cell 2c of the electrolytic bath 2' by a line containing a circulating pump P2. That is, the container bath 4 is connected at the upper part to a withdrawing line 81 of the cathode cell 2c, and is connected at the bottom to an inlet of the circulating pump P2 via a line 80. The outlet of the circulating pump P2 is connected to an inlet of the cathode cell 2c via a line 82. The container bath 4 has at the bottom a withdrawing system 9a for alkaline ionized water having a desired pH value, and the withdrawing system 9a has a water collecting means 900. The water collecting means 900 may be arbitrarily selected from, for example, a valve and a pump.

A supplying system 7a' of raw material water of alkaline ionized water is connected to the container bath 4. In the second embodiment, the raw material water is an electrolysis solution, and a sodium chloride solution of 0.1 to 0.2% is used, for example.

Upon producing alkaline ionized water according to the second embodiment, an electrolysis solution is supplied from the electrolysis solution supplying system 6b to the anode cell; an electrolysis solution as raw material water previously stored in the container bath 4 is supplied to the cathode cell 2c by the circulating pump P2; and under the conditions, electrolytic voltage is applied between the anode electrode 2e and the cathode electrode 2f.

By the application of the electrolytic voltage, the electrolysis solution is electrolyzed, an anion (chloride ion) and a cation (sodium ion) are transferred to the anode cell 2a and the cathode cell 2c, respectively, through the diaphragm 2g. Accordingly, water in the anode cell becomes acidic, and water in the cathode cell becomes alkaline, to produce alkaline ionized water in the cathode cell 2c. The alkaline ionized water is exhausted to the container bath 4 via the line 81, and then supplied to the cathode cell 2c by the circulating pump P2 via the line 82, which is again electrolyzed by the anode electrode 2e and the cathode electrode 2f.

In the invention, the above operation is repeated. Because alkaline ionized water produced in the cathode cell 2c is circulated and supplied to the cathode cell 2c to be electrolyzed by repeatedly applying electrolytic voltage, the amount of an anion in the cathode cell is decreased, and a cation is transferred from the anode cell, so that a cation is accumulated in the alkaline ionized water, the pH value of which is increased with the lapse of time. After applying electrolytic voltage for a prescribed time to obtain a desired pH value, the alkaline ionized water is withdrawn by operating the water collecting means 9a. On the other hand, the electrolysis solution supplied to pass the anode cell 2a becomes acidic water by electrolysis, which is continuously withdrawn to the outside by the acidic water withdrawing system 10.

FIG. 2-B shows another example of the second embodiment. In this example, plural electrolytic baths 2A' and 2B' each having the above-described structure (two baths are used in the figure) are arranged in series. An electrolysis solution supplying system 6b is connected to an anode cell 2a of the first electrolytic bath 2A' as described above, and the electrolysis solution is supplied to the anode cell 2a. An electrolysis solution supplying system 6b' branched from the electrolysis solution supplying system 6b is connected to an anode cell 2a of the second electrolytic bath 2B'.

Cathode cells 2c of the first electrolytic bath 2A' and the second electrolytic bath 2B' are connected to each other in series via a line 810, and a circulation system 8a is constituted with a line containing an outer container bath 4 and a circulating pump P2. That is, the container bath 4 is connected at the upper part to a withdrawing line 81 of the cathode cell 2c of the second electrolytic bath 2B', and is connected at the bottom to an inlet of the circulating pump P2 via a line 80. An outlet of the circulating pump P2 is connected to an inlet of the cathode cell 2c of the first electrolytic bath 2A' via a line 82. The container bath 4 has at the bottom a withdrawing system of alkaline ionized water having a desired pH value, and the withdrawing system has a water collecting means. The water collecting means 900 may be arbitrarily selected from, for example, a valve and a pump. As similar to the above embodiment, a supplying system 7a' of raw material water of alkaline ionized water is connected to the container bath 4.

In this example, an electrolysis solution is continuously supplied to the anode cells 2a of the first electrolytic bath 2A' and the second electrolytic bath 2B' from the electrolysis solution supplying systems 6b and 6b'; raw material water previously stored in the container bath 4 is supplied to the cathode cells 2c of the first electrolytic bath 2A' and the second electrolytic bath 2B' one by another by the circulating pump P2; and under the conditions, electrolytic voltage is applied between the anode electrodes 2e and the cathode electrodes 2f of the electrolytic baths. In the first electrolytic bath 2A' electrolysis is carried out as described above to produce alkaline ionized water in the cathode cell 2c. The alkaline ionized water is supplied to the cathode cell 2c of the second electrolytic bath 2B' via the line 810. The alkaline ionized water is similarly electrolyzed in the second electrolytic bath 2B', and a cation is accumulated in the alkaline ionized water. The alkaline ionized water is exhausted from the cathode cell 2c of the second electrolytic bath 2B' to the container bath 4 via the line 81, and is again supplied to the cathode cell 2c of the first electrolytic bath 2A' by the circulating pump P2 via the line 82, which is then again electrolyzed. The operation is repeated in the second electrolytic bath 2B'.

In FIG. 2-B, because alkaline ionized water produced in the cathode cells 2c of the plural electrolytic baths 2A' and 2B' one by another is circulated and supplied as an electrolysis solution, to be electrolyzed by repeatedly applying electrolytic voltage, a cation is accumulated in the alkaline ionized water in a short period of time, and alkaline ionized water having a high pH value can be effectively produced. When the pH value becomes a desired value, the alkaline ionized water is withdrawn by operating the water collecting means 900.

A manufacturing apparatus of electrolytic ionized water according to the invention is explained below.

Figure 4:
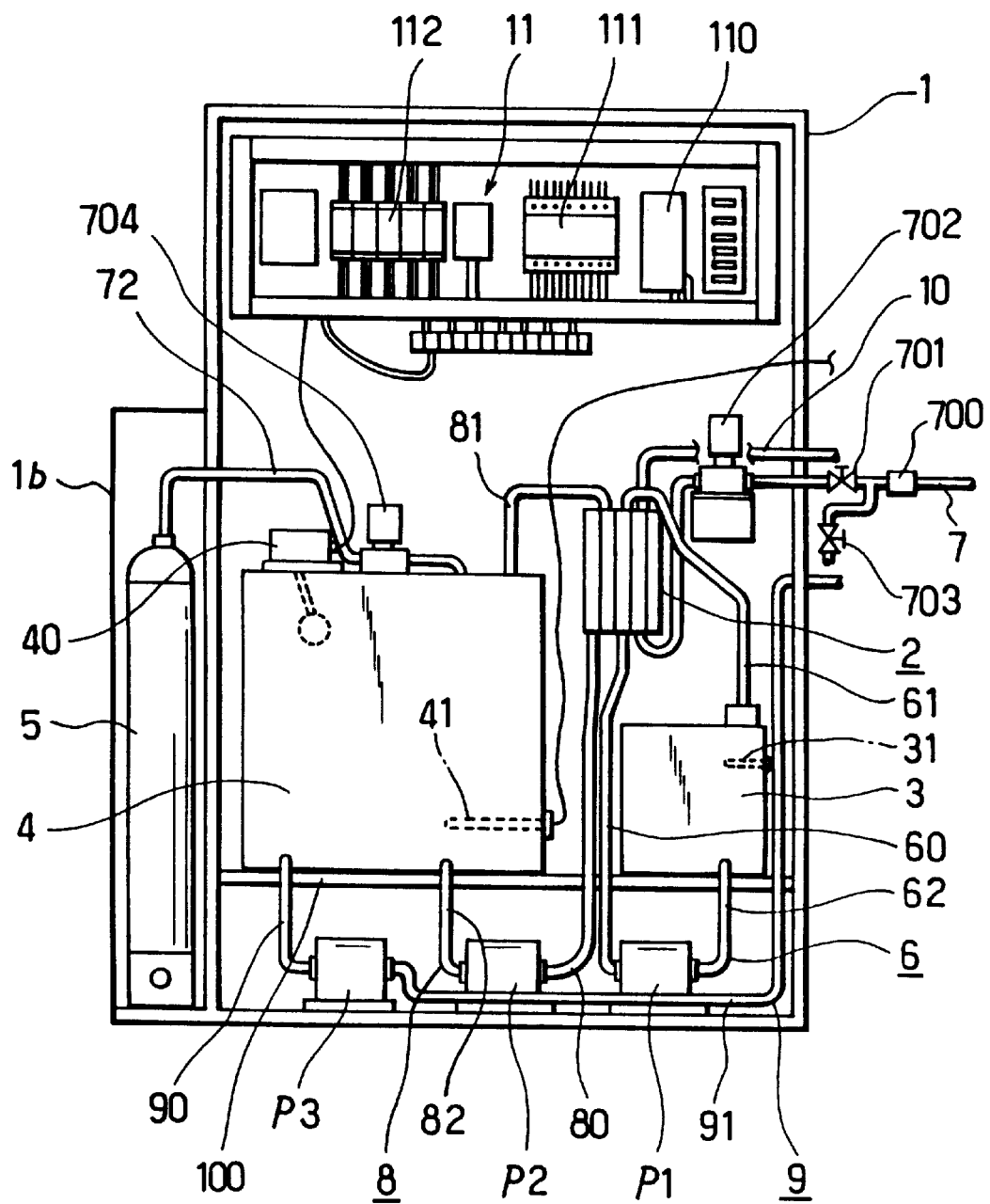
FIG. 4 is a front view of the first example.

FIGS. 3 to 7 show the first embodiment of the apparatus of the invention. The first embodiment is to conduct the most preferred first embodiment of the manufacturing method of the invention. In FIGS. 3 and 4, numeral 1 denotes a housing in the form of a box, which can be opened and closed by a lid 1a, which also serves as a control panel. A sub-housing 1b having a smaller size than the housing 1 is provided adjacent to the housing 1. The sub-housing 1b has a lid.

Numeral 2 denotes an electrolytic bath provided in the housing 1, and 3 denotes an electrolysis solution bath provided on one side of the electrolytic bath 2. Numeral 4 denotes a circulation container of alkaline ionized water provided on the other side of the electrolytic bath 2, which has a relatively larger capacity than the electrolysis solution bath 3.

Numeral 5 denotes a supplying means supplying raw material water of alkaline ionized water with adjusting its quality, a representative example of which includes a pure water manufacturing apparatus. In this example, a pure water manufacturing apparatus of the cartridge type, in which an ion exchange resin is filled in a cartridge, which is freely exchangeable, is employed, and removably attached to the sub-housing 1b.

Symbol P1 denotes an electrolysis solution circulating pump, P2 denotes an alkaline ionized water circulating pump, and P3 is a water collecting device to withdraw alkaline ionized water thus produced to the outside, which is a pump in this example. The three pumps P1, P2 and P3 are preferably electromagnetic pumps, which are arranged and fixed on the lower side of a partition plate 100 provided at the lower part of the housing 1.

Figure 6:
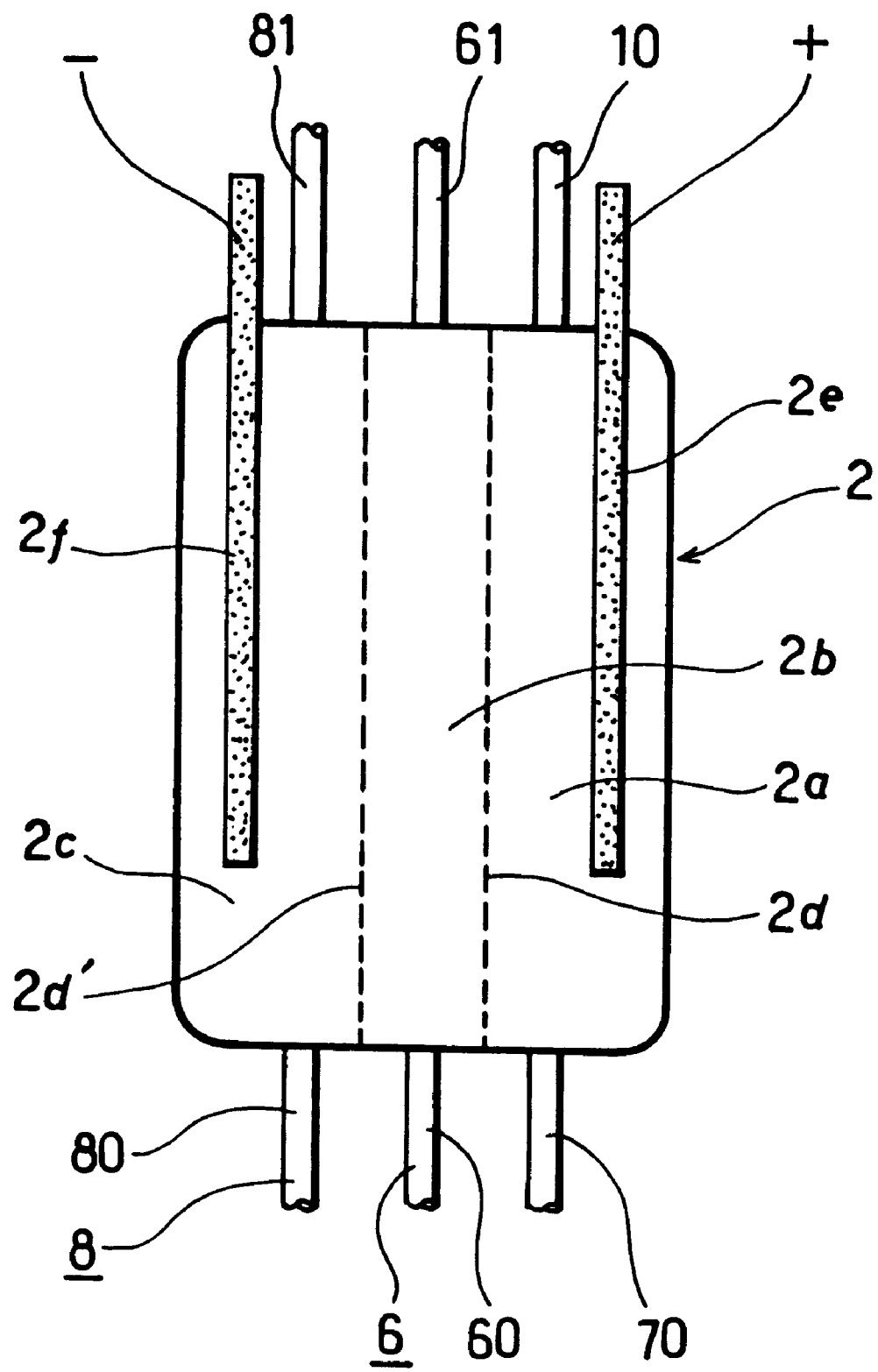
FIG. 6 is an explanatory view schematically showing an example of the electrolytic bath in the invention.

The electrolytic bath 2 has, as shown in FIG. 6, a diaphragm (anion exchange membrane) 2d and a diaphragm (cation exchange membrane) 2d' in the central part of the bath body. By the diaphragms, an intermediate cell 2b is provided on the center, and an anode cell 2a and a cathode cell 2c are provided on both sides of the intermediate cell 2b. In the anode cell 2a and the cathode cell 2c, an anode electrode 2e and a cathode electrode 2f are provided, respectively, and face each other. The anode electrode 2e and the cathode electrode 2f are connected to a direct-current power source 110 containing a rectifier attached at an upper part of the housing.

Figure 5:
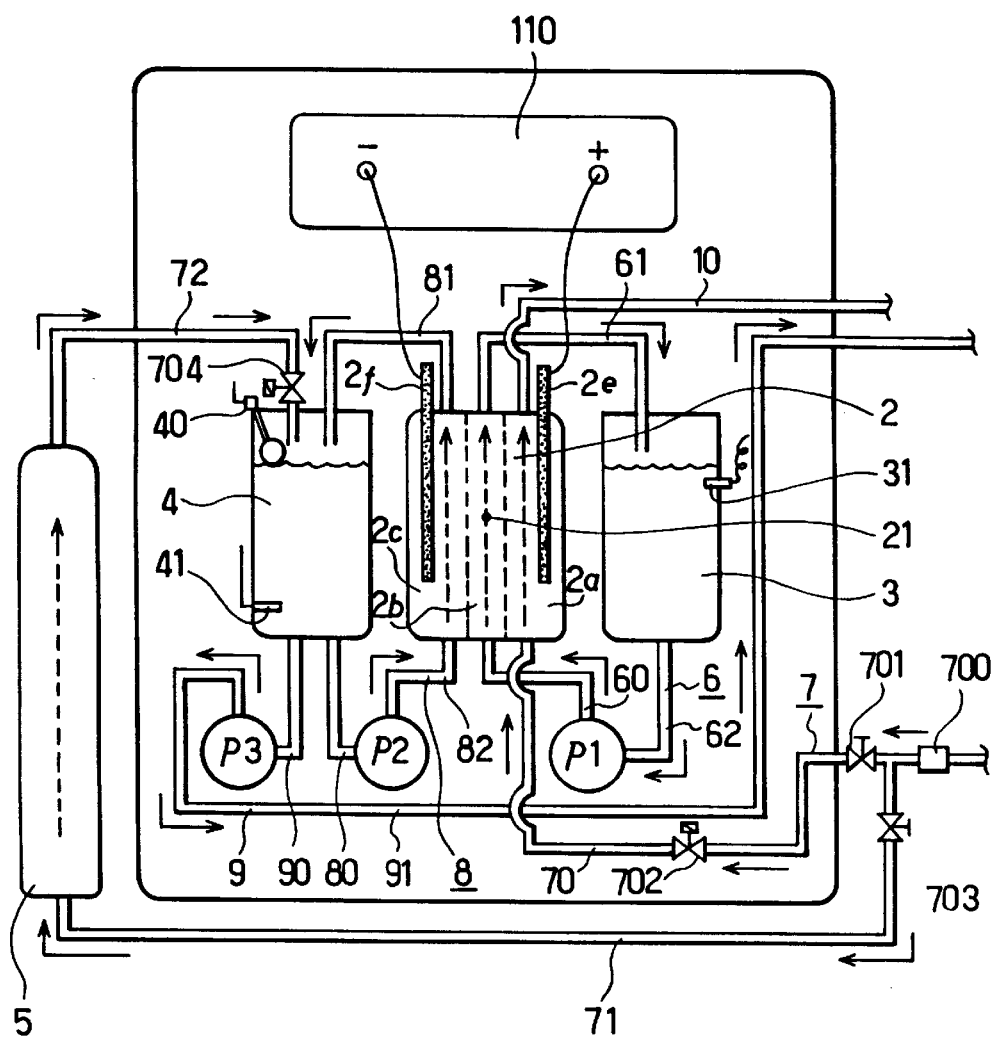
FIG. 5 is an explanatory view schematically showing the structure and the transferring system of water of the first example.

Numeral 6 is an electrolysis solution circulating line containing the circulating pump P1, which has a first line part 60, a second line part 61 and a third line part 62 as shown in FIGS. 4 and 5. The first line part 60 is connected at one end to the intermediate cell 2b of the electrolytic bath 2, and at the other end to an outlet of the circulating pump P1. The second line part 61 is connected at one end to an inlet of the electrolysis solution bath 3, and at the other end to an outlet of the intermediate cell 2b of the electrolytic bath 2. The third line part 62 is connected at one end to a lower part of the electrolysis solution bath 3, and at the other end to an inlet of the circulating pump P1.

Numeral 7 denotes a raw material water supplying line, which is introduced from the outside to the inside of the housing as shown in FIG. 5. The raw material water may be arbitrarily water for industrial use, tap water or well water. The supplying line 7 has on the upper side a letdown valve 700 to control the water pressure to the prescribed pressure, and a line part 70 at the lower side is connected to the anode cell 2a of the electrolytic bath 2. On the middle of the line part 70, a flow amount adjusting valve 701 of manually operation type or electromagnetic operation type, and a switch valve 702 for terminating supply of raw material water to the anode cell 2a on stopping the operation are provided.

In this example, a line part 71 is branched at the lower side of the letdown valve 700. The line part 71 is a supplying system of raw material water for producing alkaline ionized water, which is connected to an inlet of the supplying means 5 of raw material water of alkaline ionized water (a pure water manufacturing apparatus in this example) via a flow amount adjusting valve 703 of manually operation type or electromagnetic operation type. An outlet of the supplying means 5 of raw material water is connected to the inside of a circulation container bath 4 of alkaline ionized water via a line 72. A supplying valve 704 of electromagnetic operation type is provided on the line 72 to control the water amount in the circulation container bath 4.

Numeral 8 denotes a circulating line for accumulating an alkali ion having on its middle the circulating pump P2 of alkaline ionized water, which has a first line part 80, a second line part 81 and a third line part 82 as shown in FIG. 5.

The first line part 80 is connected at one end to a lower part of the circulation container bath 4, and at the other end to an inlet of the circulating pump P2. The second line part

81 is connected at one end to an upper part of the circulation container bath 4, and at the other end to an outlet of the cathode cell 2c of the electrolytic bath 2. The third line part 82 is connected at one end to an outlet of the circulating pump P2, and at the other end to an inlet of the cathode cell 2c of the electrolytic bath 2. Therefore, by operating the circulating pump P2, raw material water or alkaline ionized water produced in the cathode cell 2c is supplied to the cathode cell 2c via the second line part 81, the circulation container bath 4, the first line part 80 and the third line part 82, to form a circulation system.

Numeral 9 denotes a withdrawing line of alkaline ionized water having a desired pH value thus produced, which has a water collecting device (water collecting means) on its middle. As the water collecting device, the pump P3 is used to pump the water for withdrawal in this example. The withdrawing line 9 has a first line part 90 and a second line part 91. The first line part 90 is connected at one end to a lower part of the circulation container bath 4 of alkaline ionized water, and at the other end to an inlet of the water collecting pump P3. The second line part 91 is connected at one end to an outlet of the water collecting pump P3, and the other end is withdrawn from the housing 1 to the outside.

Numeral 10 denotes a withdrawing line of acidic water, which is connected at one end to an outlet of the anode cell 2a of the electrolytic bath 2, and the other end is withdrawn from the housing 1 to the outside. In some cases, a water collecting device, such as a pump, may be provided on the middle of the withdrawing line.

In FIG. 4, numeral 11 denotes a control means provided on an upper part of the housing 1. The control means 11 has, in addition to the direct-current power source 110, a relay circuit 112 and a controller 111 having a sequence circuit that controls operation of the various parts of the apparatus according to a prescribed program, an example of which is shown in FIG. 9. A pH meter 12 for indicating a desired pH value of alkaline ionized water is attached to the lid 1a.

An output of the controller 111 is electrically connected to the circulating pump P1, the circulating pump P2 of alkaline ionized water, and a driving part of the water collecting device (the water collecting pump P3 in this example), to control them by on-off operation.

Figure 7:
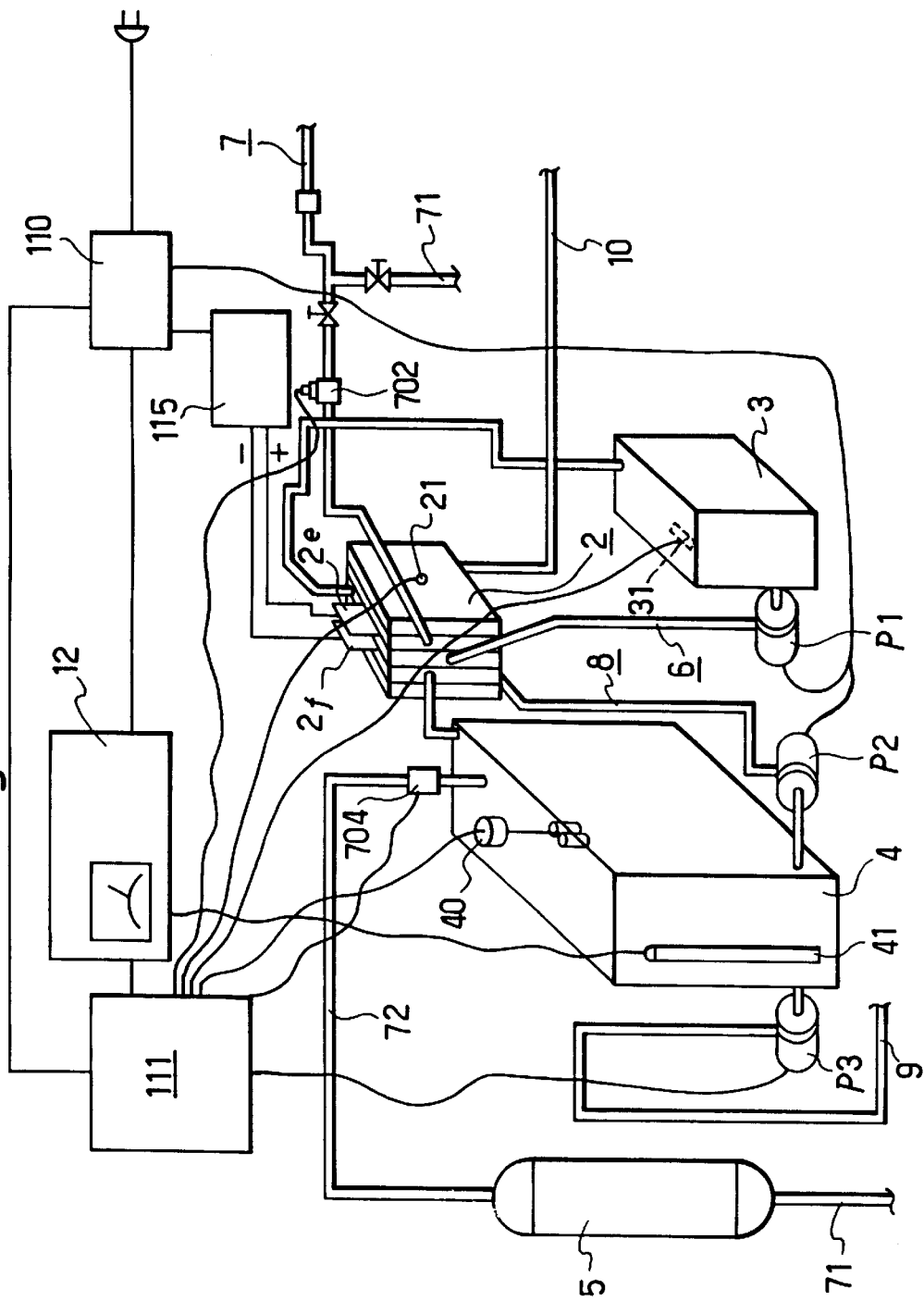
FIG. 7 is an explanatory view showing the controlling system in the invention.

As shown in FIGS. 4, 5 and 7, the circulation container bath 4 of alkaline ionized water has a means for detecting the amount of alkaline ionized water (raw material water at the start of the operation) contained in it, a representative example of which is a float switch 40, and a pH measuring device 41 detecting the pH value of alkaline ionized water is provided in the circulation container bath.

The float switch 40 is electrically connected to the controller 111, and the supplying valve 704 and the water collecting device (the water collecting pump P3 in this example) are relationally operated and controlled by a signal obtained by processing a signal from the float switch with the controller 111.

The pH measuring device 41 is connected to the pH meter 12, and continuously detects the pH value to send it as a signal. The pH meter 12 is electrically connected to the controller 111, and when the controller 111 decides that the pH value of the alkaline ionized water contained in the circulation container bath 4 for alkaline ionized water reaches the pH vale arbitrarily set in the pH meter 12, a signal is generated by the controller 111, so as at least to terminate the circulating pump P2 of alkaline ionized water, and to turn off the relay circuit of electrolytic current of the direct-current power source 110, and further to drive the water collecting device (the water collecting pump P3 in this case). In the case where the water collecting device is an electromagnetic valve, the signal opens the valve.

The electrolysis solution bath 3 has a level switch 31 as shown in FIGS. 4 and 5, and the level switch 31 is also electrically connected to the controller 111 to control on-off operation of the circulating pump P1 of the electrolysis solution and the electrolytic current relay of the direct-current power source 110.

The electrolytic bath 2 is equipped with a temperature sensor 21 detecting the temperature of the electrolysis solution as shown in FIG. 5. The temperature sensor 21 is connected to a thermometer 15 provided on the lid 1a, and is electrically connected to the controller 111. When the temperature of the electrolysis solution exceeds the prescribed temperature, it generates a signal, which automatically turns off the electrolytic current relay of the direct-current power source 110.

The lid 1a further has a power switch 16, an automatic-manual changeover switch 17, and an ammeter 19, which are connected to the controller 111 and the power source 110.

Figure 8:
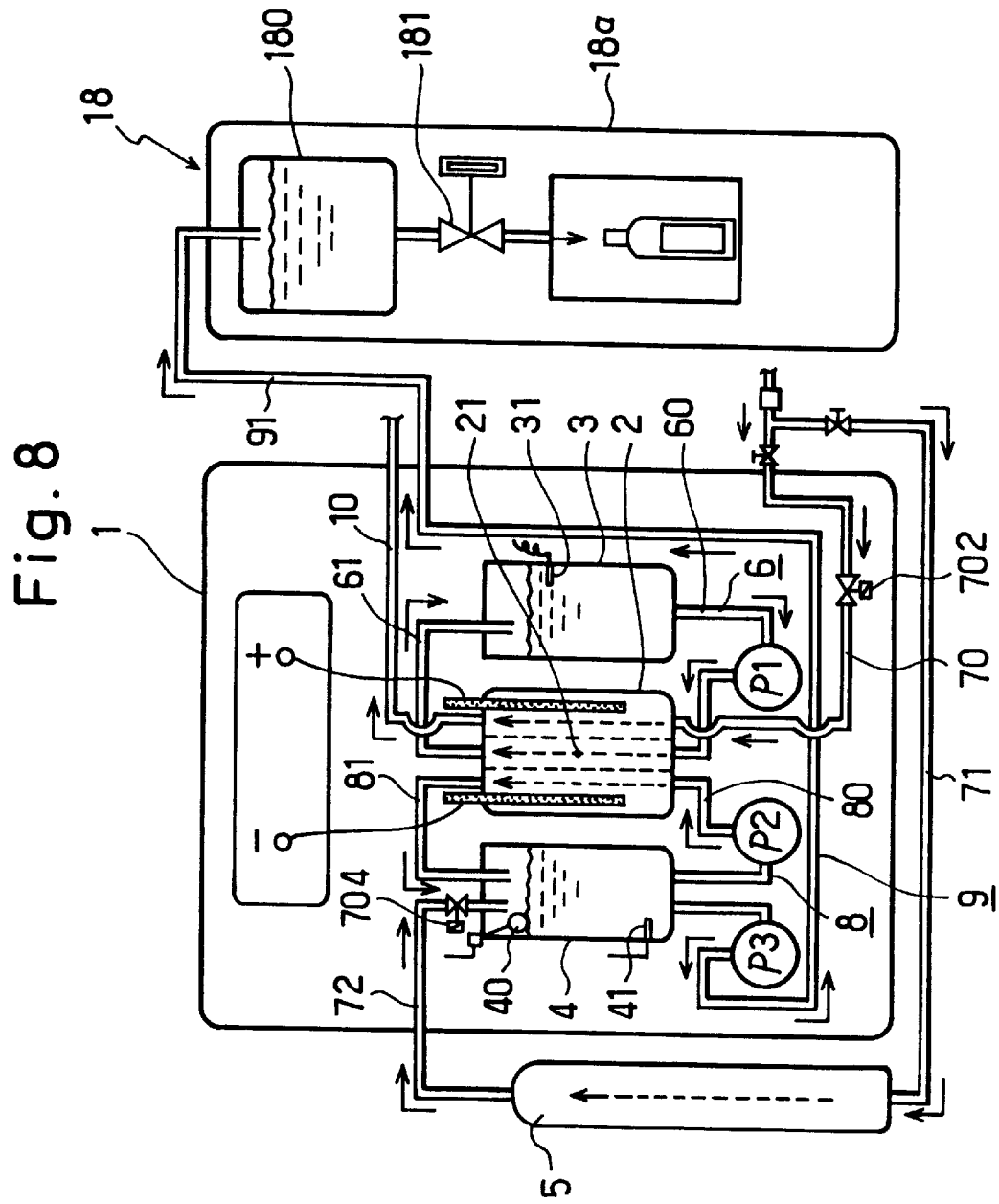
FIG. 8 is a partially cutaway view in perspective of the second example of a manufacturing apparatus of electrolytic ionized water according to the invention.

FIG. 8 shows a second example of the apparatus of the invention.

In this example, a vending machine 18 is provided outside the housing 1, and a prescribed amount of the thus produced alkaline ionized water can be withdrawn with the relation to the insertion of a coin.

The vending machine 18 contains, in a housing 18a, a container bath 180 connected to an end of the second line part 91 of the withdrawing line 9 of alkaline ionized water, and a withdrawing valve 181 for withdrawing alkaline ionized water in the container bath 180 through opening by the insertion of a coin provided at a lower part of the container bath 180.

Since the other constitutions are the same as the first example, the same symbols are attached to the same parts, and their explanations are omitted.

FIG. 9 shows a flow-sheet of an operation program by the controller 11 in the apparatus of the invention. However, this is only an example, and the program is not construed as being limited to this.

Similarly, the structures of the apparatuses shown in the figures are only some examples of the invention, but the invention is not construed as being limited to them.

In the above-described example, a pure water manufacturing apparatus is used as the supplying means 5 of raw material water for alkaline ionized water, and the line part 71 branched from the supplying line 7 of raw material water for producing acidic water is connected to be a supplying system of raw material water of alkaline ionized water, but the invention is not limited to them, and the supplying system of raw material water for alkaline ionized water may be an independent system.

Furthermore, in the example, the pure water manufacturing apparatus of the cartridge type, in which an ion exchange resin is removably filled in a cartridge, is used, but the invention is not limited to it.

As the supplying means 5 of raw material water for producing alkaline ionized water, a pure water container bath 5' of tank type or bomb type, in which pure water separately produced by an external pure water manufacturing apparatus is filled, can be used as shown in FIG. 10-A. In this case, the pure water container bath is arranged inside or outside the housing 1, and pure water is supplied to the circulation container bath 4 of alkaline ionized water by means of gravity or a pump.

In the invention, tap water may be used as raw material water for producing alkaline ionized water as described above. In this case, the line part 71 is branched from the supplying line 70 of raw material water for producing acidic water to the electrolytic bath 2, and is connected to the circulation container bath 4 via the supplying valve 704.

Figure 11:
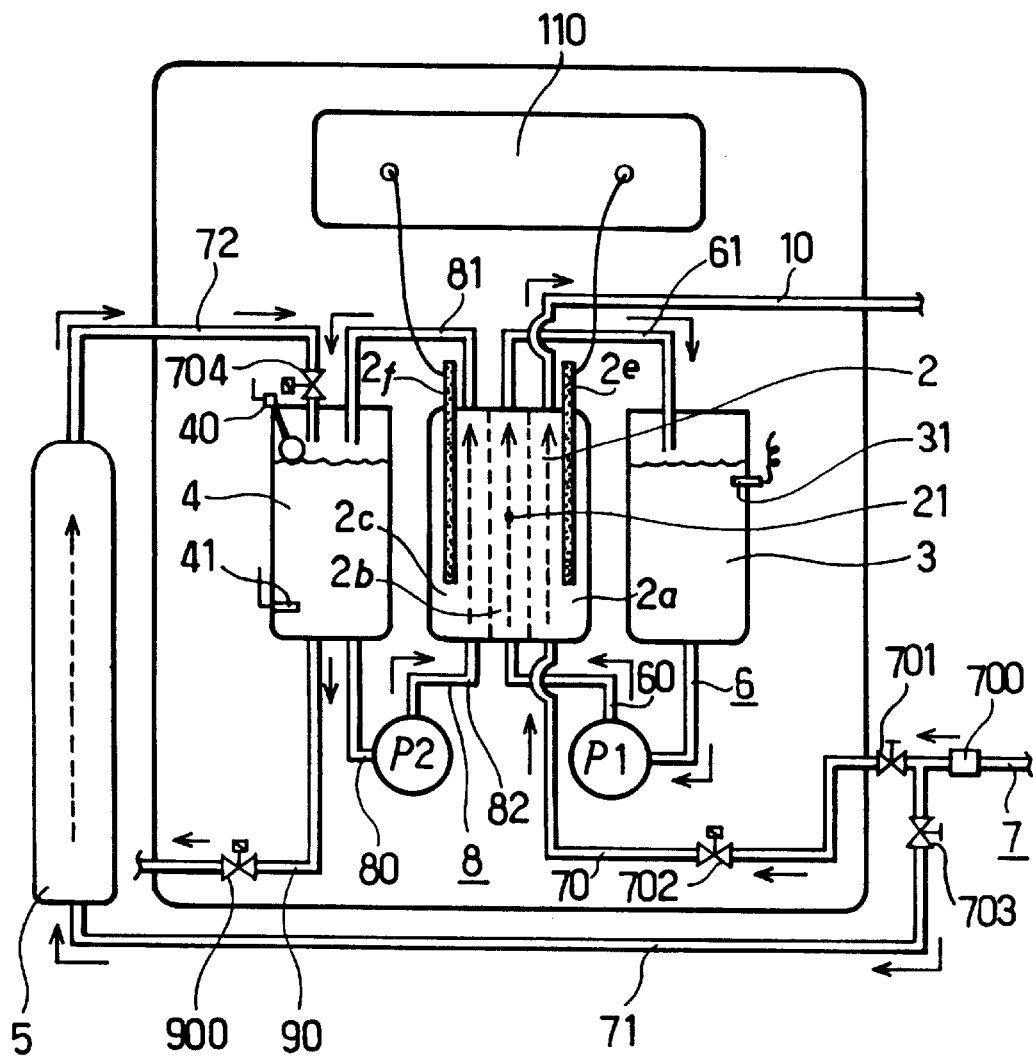
FIG. 11 is a front view of another example of the withdrawing system of alkaline ionized water in the invention

As the water collecting device (withdrawing means), a valve 900 of electromagnetic type or the like may be used instead of the pump P3 as shown in FIG. 11.

The constitutions shown in FIGS. 1-B and 2-B are installed in the housing 1 as similar to those shown in FIGS. 3 to 5. However, the number of the electrolytic baths is not limited to those shown in the figures.

The operation method and the functions of the apparatus shown in the example are explained. The case is exemplified, in which pure water is used as raw material water for producing alkaline ionized water; tap water is used as raw material water for acidic water; and a pump is used as the water collecting device of the thus produced alkaline ionized water.

Upon starting the operation, an electrolysis solution is filled in the electrolysis solution bath 3; the flow amount adjusting valve 703 is opened to supply tap water to the supplying means 5 (pure water manufacturing apparatus in this example) of raw material water for producing alkaline ionized water, so that salt ions are removed to produce pure water, which is stored in a prescribed amount in the circulation container bath 4.

At this time, even when the flow amount adjusting valve 701 is opened, tap water is not supplied to the electrolytic bath 2 since the switch valve 702 on the line part 70 is closed.

After completing the preparation for operation, a desired pH value of alkaline ionized water to be produced is set on the pH meter 12. By selecting the automatic operation switch, the operation of the apparatus is started by a signal from the controller 111 as shown in the program of FIG. 9.

In the first step, the circulating pump P2 provided on the circulating line 8 for accumulation of alkaline ions and the circulating pump P1 provided on the electrolysis solution circulating line 6 are operated, and at the same time, electrolytic current is supplied from the power source 110, and the switching valve 702 on the line part 70 is opened.

By the operation of the circulating pump P2, pure water is withdrawn from the circulation container bath 4 via the first line part 80, and exhausted from the circulating pump P2. It is supplied to the cathode cell 2c of the electrolytic bath 2 via the third line part 82, and then returned from the cathode cell 2c to the circulation container bath 4 via the second line part 81.

By the operation of the circulating pump P1, the electrolysis solution is withdrawn from the electrolysis solution bath 3 and supplied to the intermediate cell 2b of the electrolytic bath 2 via the third line part 62 and the first line part 60, and then returned from the intermediate cell 2b to the electrolysis solution bath 3 via the second line part 61, to constitute a circulation system.

By opening the switching valve 702, tap water, which is evacuated to a prescribed pressure by the letdown valve 700, is supplied to the anode cell 2a of the electrolytic bath 2.

In the electrolytic bath 2, electrolytic voltage is applied between the anode electrode 2e and the cathode electrode 2f, and water containing an electrolyte is electrolyzed as described in the explanation of FIG. 1-A. Pure water becomes alkaline ionized water in the cathode cell 2c, and then returned to the circulation container bath 4 by the circulation system. It is again supplied to the cathode cell 2c of the electrolytic bath 2 by the circulating pump P2, and the operation, in which it is electrolyzed, is repeated. Accordingly, the alkaline ionized water is repeatedly subjected to application of electrolytic voltage, and its pH value is increased.

On the other hand, tap water supplied to pass the anode cell 2a becomes acidic water by electrolysis, and is continuously withdrawn to the outside by the acidic water withdrawing line 10.

The pH value of the alkaline ionized water in the course of production is continuously measured by the pH measuring device 41 provided in the circulation container bath 4. Its signal is sent to the pH meter 12 to be continuously indicated, and is inputted from the pH meter 12 to the controller 111 to compare and evaluate its level. When it is assumed that the set value of the pH meter 12 is 12.5, for example, the alkaline ionized water is repeatedly circulated between the circulation container bath 4 and the cathode cell 2c, and the operation, in which electrolytic voltage is repeatedly applied, is continued until the pH value reaches this value.

The amount of the electrolysis solution in the electrolysis solution bath 3 in the course of production is continuously detected by the level switch 31 of the electrolysis solution bath 3, and the signal from this is inputted to the controller 111 to evaluate as to whether or not it is normal. When the amount of the electrolysis solution is less than a prescribed amount, the operation of the circulating pump P1 and the supply of electrolytic current are terminated.

At the same time, the temperature of the electrolytic bath 2 in the course of production is continuously detected by the temperature sensor 21 and inputted into the controller 111, which is then compared to the temperature previously set. Assuming that the set temperature is 60° C., when the temperature detected by the temperature sensor 21 is 60° C. or less, the operation is continued, and when it exceeds 60° C., the supply of electrolytic current is terminated.

In the invention, alkaline ionized water produced in the cathode cell 2c of the electrolytic bath 2 itself is repeatedly supplied to the cathode cell 2c of the electrolytic bath 2, so as to be subjected to application of electrolytic voltage. Accordingly, a cation is effectively accumulated in the alkaline ionized water, and its pH value is increased. When it reaches the desired set pH value, for example pH 12.5, the signal is inputted from the pH measuring device 41 to the pH meter 12 and the controller 111, and a signal is generated by the controller 111, so as to terminate the operation of the circulating pump P2 and the supply of electrolytic current, and to close the switch valve 702 on the supplying line part 70.

By the termination of the circulating pump P2, the circulation of the alkaline ionized water between the electrolytic bath 2 and the circulation container bath 4 is terminated, and the alkaline ionized water having a high pH value produced in a prescribed amount is stored in the circulation container bath 4. The supply of tap water to the anode cell of the electrolytic bath 2 is also terminated, and the electrolysis by the electrodes is terminated.

When the above state is confirmed, the water collecting pump P3 is operated by a signal from the controller 111. The alkaline ionized water having a high pH value stored in the circulation container bath 4 is withdrawn to the outside through the withdrawn line 9. The withdrawn amount is detected by the float switch 40, and when the float switch 40 is turned off after the withdrawal of a prescribed amount, the operation of the water collecting pump P3 is terminated by a signal from the controller 111. Subsequently, the supplying valve 704 is opened, and thus pure water is supplied to the circulation container bath 4 via the supplying line 72 from the pure water manufacturing apparatus. When the float switch 40 is turned on, the supplying valve 704 is turned off, so that a prescribed amount of alkaline ionized water diluted with pure water (pure water when the whole amount of alkaline ionized water is withdrawn from the circulation container bath 4) is stored in the circulation container bath 4.

After reaching this state, the operation returns to the first step, and the production of alkaline ionized water is initiated. After that, the above procedures are repeated, so as to intermittently produce strongly alkaline ionized water and to continuously produce acidic water.

In the second example, alkaline ionized water withdrawn to the outside via the withdrawing line 9 is supplied to and stored in the container bath 180. By inserting a coin, the withdrawing valve 181 is opened for a prescribed period of time, and the alkaline ionized water is withdrawn and sold.

In the invention, the resulting alkaline ionized water is circulated and supplied to the cathode cell 2c of the electrolytic bath 2 by using the circulation container bath 4 of alkaline ionized water and the circulating pump P2. Therefore, high alkaline ionized water having a pH value exceeding 12.0 and redox potential exceeding −800 mV can be produced by arbitrarily changing the time of electrolysis. Because a prescribed amount of alkaline ionized water stored in the circulation container bath 4 is circulated to accumulate a cation to obtain a high pH value, it does not suffer from influence of change in electrolytic current due to change in concentration and temperature of the electrolysis solution, and therefore alkaline ionized water of good precision with less fluctuate in pH vale can be produced.

The invention is economical because even when pure water is used, it is supplied only to the circulation container bath 4, and inexpensive water, such as water for industrial use, tap water and well water, may be supplied to the anode cell side, at which acidic water is produced.

After the withdrawal of alkaline ionized water having a desired pH value, raw material water corresponding to the loss in weight is supplied to the circulation container bath 4, so that a constant amount of the resulting alkaline ionized water is circulated between the circulation container bath 4 and the cathode cell 2c by the circulating pump P2, and thus the electrolytic bath 2 may be of small size and low capacity. Therefore, the incidental electrolysis solution bath 3 may be a compact one, and a large amount of alkaline ionized water can be produced by a relatively compact apparatus.

Because alkaline ionized water produced according to the invention has a high pH value exceeding 12.0, excellent deterging effect can be obtained in addition to disinfection effect. Acidic water continuously produced at the same time is one having pH value of 2.7 or less, and functions of sterilization, disinfection and deodorizing are exhibited by the effect of hypochlorious acid formed by electrolysis.

Specific examples producing electrolytic ionized water according to the invention are described below.

EXAMPLE 1

1) As the apparatus, one shown in FIGS. 3 to 9 was used. An electrolytic bath having an electrolysis solution cell having a capacity of 60 ml at the center, and an anode cell 2a and a cathode cell 2c each having a capacity of 75 ml on both sides was used. As the electrolysis solution bath, a container made of polyvinyl chloride having a capacity of 10 L was used. As the circulation container bath of the alkaline ionized water, a container made of polyvinyl chloride having a capacity of 30 L was used. As the pure water manufacturing means, a pure water manufacturing apparatus filled with an ion exchange resin having a resin capacity of 5 L and a pure water manufacturing capacity of 950 L/C was used.

A magnet pump of a delivery amount of 6 L per minute was used as the electrolysis solution circulating pump, a magnet pump of a delivery amount of 6 L per minute was used as the alkaline ionized water circulating pump, and a magnet pump of a delivery amount of 10 L per minute was used as the water collecting pump for alkaline ionized water.

Before the production, 8 L of a 20% sodium chloride solution was stored in the electrolysis solution bath, and 20 L of pure water produced by the pure water manufacturing apparatus was stored in the circulation container bath.

Upon production, pure water (the resulting alkaline ionized water after starting the production) was circulated and supplied from the circulation container bath to the cathode cell at a flow rate of 1 L/min by operating the circulating pump; tap water was supplied to the anode cell at a flow rate of 0.5 L/min; and the 20% sodium chloride solution was supplied from the electrolysis solution bath to the electrolysis solution cell at a flow rate of 1 L/min by operating the electrolysis solution circulation pump. Electrolytic voltage of 12 V was applied between the cathode electrode and the anode electrode.

When the voltage applying time was continuous 1.5 hours as a preliminary experiment, the resulting alkaline ionized water (which was called as comparative ionized water) had pH 12.0 and a redox potential of −620 mV, and the acidic water had pH 2.6 in an amount of 45 L.

When the voltage applying time was then changed to continuous 3.2 hours and continuous 5 hours, the following two kinds of alkaline ionized water were obtained. The alkaline ionized water was withdrawn in an amount of 19.5 L by operating the water collecting pump.
(First Ionized Water)

It was alkaline ionized water obtained by continuously applying voltage for 3.2 hours. It had pH 12.3 and a redox potential of −850 mV. The amount of the acidic water withdrawn from the anode cell was 96 L and its pH was 2.6.
(Second Ionized Water)

It was alkaline ionized water obtained by continuously applying voltage for 5 hours. It had pH 12.5 and a redox potential of −930 mV. It was expected that the circulation number of the alkaline ionized water was about 15. The amount of the acidic water withdrawn from the anode cell was 150 L and its pH was 2.6.

2) For comparison, alkaline ionized water was produced by the conventional method. Specifically, the same constitution as the above-described apparatus was employed, except that the water circulation container bath, the circulating pump of alkaline ionized water, and the water collecting pump were removed from the above-described apparatus; pure water was supplied from the pure water manufacturing apparatus directly to the cathode cell; and alkaline ionized water produced in the cathode cell was collected as it is.

As the production conditions, pure water was supplied to the cathode cell at a flow rate of 1 L/min; tap water was supplied to the anode cell at a flow rate of 0.5 L/min; a 20% sodium chloride solution was supplied from the electrolysis solution bath to the electrolysis solution cell at a flow rate of 1 L/min by operating the electrolysis solution circulating pump; and electrolytic voltage of 12 V was applied between the cathode electrode and the anode electrode.

In this conventional method, the pH value of the collected ionized water theoretically becomes constant irrespective to the time of applying voltage. However, when electrolysis was actually conducted in a continuous manner, a part of electric energy of electrolysis was changed into heat energy to increase the temperature of the electrolysis solution. When the temperature of the electrolysis solution was increased, electric current was easy to pass it, which resulted in different electrolysis conditions from the start point. Taking this into consideration, the decision was made after continuous application of voltage for 5 hours.

The collected alkaline ionized water (which was called as conventional ionized water) had pH 11.5 and a redox poten- As test bacteria, *Escherichia coil* ATCC 43895 (colon bacillus, serium type 0157:H7, verotoxin I and II forming strain) was used.

As the bacteria liquid, a culture liquid obtained by culturing the bacteria in a normal bouillon culture medium added with 0.2% of meat extract at 35° C. for 10 to 24 hours was used.

In the test operation, 1 ml of the bacteria liquid was added to 10 ml of the sample. After it was acted at 20° C. for 30 seconds, 1 minute or 5 minutes, 1 ml of each was added to 9 ml of an SCDLP culture medium to measure the number of live bacteria. The number of live bacteria was measured by the agar flat plate culturing method using a SCDLPA culture medium (35° C. 48-hour culturing). Sterilized purified water was subjected to the same test as a control test. The acted time was 5 minutes.

The results obtained are shown in Table 1 below.

TABLE 1

| | | Number of live bacteria per 1 ml of test liquid | | | |
|---|---|---|---|---|---|
| Test bacteria | Test liquid | Immediately after start | After 30 seconds | After 1 minute | After 5 minutes |
| Colon bacillus 0517 | Second ionized water pH 12.5 | $5.1 \times 10^7$ | <10 | <10 | <10 |
| | Comparative ionized water pH 12.0 | $5.8 \times 10^7$ | $1.9 \times 10^7$ | $2.1 \times 10^7$ | $1.4 \times 10^7$ | tial of −600 mV. The amount of the acidic water withdrawn from the anode cell was 150 L, which had pH 2.6.

It is understood from the above that in the invention, alkaline ionized water having an extremely high pH vale can be stably obtained in a short period of time in comparison to the conventional method.

3) Alkaline ionized water having a higher pH value was produced by using the above-described apparatus. Under the above-described conditions, when the application of voltage was conducted for continuous 9.4 hours, alkaline ionized water having pH 13.0 was obtained. As a result of application of voltage for continuous 30 hours, super alkaline ionized water having pH 13.4 and a redox potential of −1,200 mV was obtained.

A performance test of the thus produced alkaline ionized water was conducted.

1. Results of Deterging Test

A rust preventing oil (animal and vegetable series oil) was coated with a brush on a sample piece of 150 mm×70 mm×0.8 mm of a cold rolling steel plate (SPCC-SD), and was allowed to stand in a room at a temperature of 25° C. and a humidity of 50%. After 24 hours, the second ionized water (pH 12.5) and the conventional ionized water (pH 11.5) each were sprayed for 5 minutes on the test piece, which was held horizontally, and the deterging power was determined from the removal ratio of the oil.

As a result, the removal ratio of the oil in the case of the second ionized water was 100%, and the removal ratio of the oil in the case of the conventional ionized water was 50%.

2. Results of Disinfection Test

1) Re Colon bacillus

The second ionized water and the comparative ionized water were used as samples (test liquids), to which a bacteria liquid of colon bacillus was added. The number of live bacteria in the test liquid was measured with the lapse of time.

It is understood from Table 1 that the alkaline ionized water of the invention had an extremely high sterilization effect. The comparative ionized water having pH 12.0 was poor in sterilization effect. It is apparent from the above that the conventional ionized water having pH 11.5 is further poor in sterilization effect.

2) Re *Pseudomonas aeruginosa, Salmonella enteritidis* and *Staphylococcus aureus*

The first ionized water, the second ionized water and the comparative ionized water were used as samples (test liquids), to which a bacteria liquids of *Pseudomonas aeruginosa, Salmonella typhimurium* and *Staphylococcus aureus* were added. The samples were stored at 20° C., and the number of live bacteria in the test liquid was measured with the lapse of time.

As test bacteria, *Pseudomonas aeruginosa* IFO 13275, *Salmonella enteritidis* IFO 3313 and *Staphylococcus aureus* IFO 12732 were used.

As the bacteria liquids, culture liquids obtained by culturing the bacteria in a normal bouillon culture medium added with 0.2% of meat extract at 35° C. for 10 to 24 hours was used.

In the test operation, 1 ml of the bacteria liquid was added to 10 ml of the sample. It was stored at 20° C. After it was acted for 30 seconds, 5 minutes or 15 minutes, 1 ml of each was added to 9 ml of an SCDLP culture medium to measure the number of live bacteria. The number of live bacteria was measured by the pour-plate culture method using a SCDLPA culture medium (35° C. 48-hour culturing). Sterilized purified water was subjected to the same test as a control test. The acted time was 15 minutes.

The results obtained are shown in Table 2 below.

TABLE 2

| Test bacteria | Test liquid | Immediately after start | After 30 seconds | After 5 minutes | After 15 minutes |
|---|---|---|---|---|---|
| Pseudomonas aeruginosa | First ionized water pH 12.3 | $8.0 \times 10^7$ | $1.4 \times 10^7$ | $1.1 \times 10^6$ | 80 |
| | Second ionized water pH 12.5 | $2.6 \times 10^7$ | $4.9 \times 10^2$ | <10 | <10 |
| | Comparative ionized water pH 12.0 | $8.0 \times 10^7$ | $1.6 \times 10^7$ | $9.4 \times 10^6$ | $9.5 \times 10^5$ |
| Salmonella enteritidis | First ionized water pH 12.3 | $5.2 \times 10^7$ | $1.7 \times 10^6$ | $1.2 \times 10^5$ | $8.6 \times 10^2$ |
| | Second ionized water pH 12.5 | $1.2 \times 10^7$ | <10 | <10 | <10 |
| | Comparative ionized water pH 12.0 | $5.2 \times 10^7$ | $1.4 \times 10^7$ | $7.8 \times 10^6$ | $6.3 \times 10^6$ |
| Staphylococcus aureus | First ionized water pH 12.3 | $1.2 \times 10^8$ | $1.1 \times 10^8$ | $1.1 \times 10^8$ | $8.0 \times 10^7$ |
| | Second ionized water pH 12.5 | $4.6 \times 10^7$ | $3.9 \times 10^7$ | $3.0 \times 10^7$ | $7.0 \times 10^6$ |
| | Comparative ionized water pH 12.0 | $1.2 \times 10^8$ | $1.2 \times 10^8$ | $1.3 \times 10^8$ | $9.6 \times 10^7$ |

It is understood from Table 2 that the first ionized water and the second ionized water had an extremely high sterilization effect. The comparative ionized water was poor in sterilization effect. Because the conventional ionized water had a lower pH value than the comparative ionized water, it is apparent that the conventional ionized water is further poor in sterilization effect.

EXAMPLE 2

Three of the electrolytic baths in Example 1 were connected in series to form a multi-stage system shown in FIG. 1-B, and the production of alkaline ionized water was conducted by using this system.

The production conditions were the same as in Example 1. As a result, alkaline ionized water obtained by applying voltage for continuous 1 hour had pH 12.3 and a redox potential of −850 mV. The amounts of the acidic water withdrawn from each of the anode cells were each 30 L, i.e., 90 L in total, each of which had pH 2.6.

The alkaline ionized water obtained after applying voltage for continuous 1.7 hours had pH 12.5 and a redox potential of −930 mV. The amounts of the acidic water withdrawn from each of the anode cells were 51 L (153 L in total), each of which had pH 2.6.

It is understood from the above results that strongly alkaline ionized water exceeding pH 12.0 can be produced in a shorter period of time than Example 1.

EXAMPLE 3

Electrolytic ionized water was produced according to the second embodiment of the invention. The apparatus shown in FIG. 2-A was used.

As the electrolytic bath, a two-cell type bath having a 100 ml anode cell on one side and a 105 ml cathode cell on the other side was used. As the electrolysis solution bath, a container made of polyvinyl chloride having a capacity of 10 L was used. As the circulation container bath of the alkaline ionized water, a container made of polyvinyl chloride having a capacity of 30 L was used. A diaphragm pump of a delivery amount of 3.2 ml per minute was used as the electrolysis solution supplying pump, a magnet pump of a delivery amount of 6 L per minute was used as the alkaline ionized water circulating pump, and a magnet pump of a delivery amount of 10 L per minute was used as the water collecting pump for alkaline ionized water.

Before the production, 8 L of a 20% sodium chloride solution was stored in the electrolysis solution bath, and a 0.13% sodium chloride solution was stored in the circulation container bath.

Upon production, the electrolysis solution (the resulting alkaline ionized water after starting the production) was circulated and supplied from the circulation container bath to the cathode cell at a flow rate of 1 L/min by operating the circulating pump, and tap water added with 3.2 ml/min of 20% sodium chloride solution was supplied to the anode cell at a flow rate of 0.5 L/min by the electrolysis solution supplying pump. Electrolytic voltage of 30 V was applied between the cathode electrode and the anode electrode. Two kinds of alkaline ionized water were obtained by setting the voltage applying time to continuous 13 hours and continuous 20 hours.

(1) When the voltage applying time was continuous 13 hours, the resulting alkaline ionized water had pH 12.3 and a redox potential of −850 mV, and the acidic water withdrawn from the anode cell had pH 3.2 in an amount of 390 L. (2) When the voltage applying time was continuous 20 hours, the resulting alkaline ionized water had pH 12.5 and a redox potential of −930 mV, and the acidic water withdrawn from the anode cell had pH 3.2 in an amount of 600 L.

It is understood from the results that strongly alkaline ionized water having pH exceeding 12.0 can be produced although the efficiency is inferior to the first example.

EXAMPLE 4

Electrolytic ionized water was produced by using two electrolytic baths shown in Example 3 to form the system of FIG. 2-B.

As a result, the alkaline ionized water obtained by applying voltage for continuous 6.5 hours had pH 12.3 and a redox potential of −850 mV. The amounts of the acidic water withdrawn from each of the anode cells each were 195 L (390 L in total), which had pH 2.6. The alkaline ionized water obtained by applying voltage for continuous 10 hours had pH 12.5 and a redox potential of −930 mV. The amounts of the acidic water withdrawn from each of the anode cells each were 300 L (600 L in total), which had pH 2.6.

It is understood from the results that strongly alkaline ionized water exceeding pH 12.0 can be produced in a shorter period of time than the third example.

What is claimed is:

1. A manufacturing method of alkaline ionized water comprising applying an electrolytic voltage between a cathode electrode and an anode electrode inside an electrolytic bath with continuously supplying an aqueous solution containing an electrolyte to said electrolytic bath, so as to produce alkaline ionized water through electrolysis of said aqueous solution containing an electrolyte, wherein an electrolytic bath having a three-cell configuration having a cathode cell, an intermediate cell and an anode cell, which are separated by a pair of diaphragms, is used, raw material water for production of acidic water is supplied to said anode cell, pure water is fed to said cathode cell, and an electrolysis solution is circulated and supplied to said intermediate cell, so as to produce alkaline ionized water in said cathode cell of said electrolytic bath; an operation, where said alkaline ionized water thus obtained is again supplied to said cathode cell and is subjected to application of electrolytic voltage, is repeated to accumulate a cation; supply of alkaline ionized water produced in said cathode cell to said cathode cell is carried out with a circulation system, in which said alkaline ionized water is withdrawn from said cathode cell and supplied to said cathode cell by a pump, with storing the same in a container equipped outside said electrolytic bath; and said supply of said alkaline ionized water produced in said cathode cell and said application of an electrolytic voltage are repeated until a pH value of said alkaline ionized water reaches pH 12.0.

2. A manufacturing method as in claim 1, wherein plural electrolytic baths each having a three-cell configuration having a cathode cell, an intermediate cell and an anode cell, which are separated by a pair of diaphragms, are used in series; raw material water for production of acidic water is supplied to said anode cells of each of said electrolytic baths; and an electrolysis solution is circulated and supplied to said intermediate cells of each of the electrolytic baths. Supply of alkaline ionized water produced in said cathode cell to said cathode cell is carried out with an circulation system, in which said alkaline ionized water withdrawn from said cathode cell of the uppermost electrolytic bath is successively supplied to said cathode cell of the next lower electrolytic bath, and said alkaline ionized water withdrawn from said cathode cell of the lowermost electrolytic bath is supplied to said cathode cell of the uppermost electrolytic bath by a pump, with storing the same in a container equipped outside said electrolytic baths.

* * * * *